(12) United States Patent
Kanno et al.

(10) Patent No.: US 9,494,862 B2
(45) Date of Patent: Nov. 15, 2016

(54) RESIST UNDERLAYER FILM FORMING COMPOSITION CONTAINING SILICON HAVING SULFONE STRUCTURE AND AMINE STRUCTURE

(71) Applicant: NISSAN CHEMICAL INDUSTRIES, LTD., Tokyo (JP)

(72) Inventors: Yuta Kanno, Toyama (JP); Kenji Takase, Toyama (JP); Makoto Nakajima, Toyama (JP); Satoshi Takeda, Toyama (JP); Hiroyuki Wakayama, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/407,895

(22) PCT Filed: Jun. 19, 2013

(86) PCT No.: PCT/JP2013/066826
§ 371 (c)(1),
(2) Date: Dec. 12, 2014

(87) PCT Pub. No.: WO2013/191203
PCT Pub. Date: Dec. 27, 2013

(65) Prior Publication Data
US 2015/0159045 A1  Jun. 11, 2015

(30) Foreign Application Priority Data
Jun. 20, 2012 (JP) .................. 2012-138960

(51) Int. Cl.
| | | |
|---|---|---|
| *G03F 7/075* | (2006.01) | |
| *G03F 7/30* | (2006.01) | |
| *G03F 7/32* | (2006.01) | |
| *G03F 7/36* | (2006.01) | |
| *G03F 7/38* | (2006.01) | |
| *G03F 7/40* | (2006.01) | |
| *G03F 7/09* | (2006.01) | |
| *C07F 7/18* | (2006.01) | |
| *C08G 77/00* | (2006.01) | |
| *C08G 77/26* | (2006.01) | |
| *C09D 183/08* | (2006.01) | |
| *H01L 21/027* | (2006.01) | |
| *H01L 21/311* | (2006.01) | |

(52) U.S. Cl.
CPC .......... *G03F 7/0752* (2013.01); *C07F 7/1804* (2013.01); *C07F 7/1836* (2013.01); *C08G 77/26* (2013.01); *C08G 77/80* (2013.01); *C09D 183/08* (2013.01); *G03F 7/0755* (2013.01); *G03F 7/0757* (2013.01); *G03F 7/091* (2013.01); *G03F 7/094* (2013.01); *G03F 7/30* (2013.01); *G03F 7/322* (2013.01); *G03F 7/325* (2013.01); *G03F 7/36* (2013.01); *G03F 7/38* (2013.01); *G03F 7/40* (2013.01); *H01L 21/0274* (2013.01); *H01L 21/31133* (2013.01)

(58) Field of Classification Search
None
See application file for complete search history.

(56) References Cited

U.S. PATENT DOCUMENTS 3,801,572 A    4/1974 Berger
3,816,494 A *  6/1974 Berger .......................... 556/418

FOREIGN PATENT DOCUMENTS

| CN | 101104622 A | 1/2008 |
| JP | S61-112086 A | 5/1986 |
| JP | 2003-246947 A | 9/2003 |
| JP | 2005-112732 A | 4/2005 |
| JP | 2009-244722 A | 10/2009 |
| WO | 2010/071155 A1 | 6/2010 |
| WO | 2011/033965 A1 | 3/2011 |
| WO | 2012/050065 A1 | 4/2012 |

OTHER PUBLICATIONS

English abstract for CN 101104622A (Yan et al) as provided by American Chemical Society (2008).*

(Continued)

*Primary Examiner* — Sin Lee
(74) *Attorney, Agent, or Firm* — Oliff PLC

(57) ABSTRACT

A resist underlayer film forming composition for lithography, including: as a silane, at least one among a hydrolyzable organosilane, a hydrolysis product thereof, and a hydrolysis-condensation product thereof, wherein the silane includes the silane compound of Formula (1-a) or Formula (1-b):

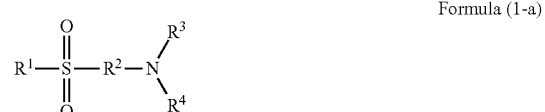

Formula (1-a)

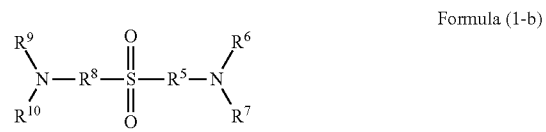

Formula (1-b)

A method for producing a semiconductor device, including: applying the resist underlayer film forming composition onto a semiconductor substrate and baking the composition to form a resist underlayer film; applying a composition for a resist onto the film to form a resist film; exposing the resist film to light; developing the resist film after exposure to obtain a patterned resist film; etching the resist underlayer film according to a pattern of the patterned resist film; and processing the semiconductor substrate according to a pattern of the resist film and the resist underlayer film.

9 Claims, 1 Drawing Sheet

(56) References Cited

OTHER PUBLICATIONS

Megia-Fernandez et al ("Non-Magnetic and Magnetic Supported Copper (I) Chelating Adsorbents as Efficient Heterogeneous Catalysts and Copper Scavengers for Click Chemistry", Advanced Synthesis $ Catalysis (2010), vol. 352, issue 18, p. 3306-3320).*

Machine-assisted English translation for JP2003-246947 provided by JPO (2003).*

Sep. 10, 2013 Written Opinion issued in International Application No. PCT/JP2013/066826.

Sep. 10, 2013 International Search Report issued in Application No. PCT/JP2013/066826.

\* cited by examiner ly hydrophilic using a silane coupling agent
having a sulfonyl group (see Patent Document 2).

RESIST UNDERLAYER FILM FORMING COMPOSITION CONTAINING SILICON HAVING SULFONE STRUCTURE AND AMINE STRUCTURE

TECHNICAL FIELD

The present invention relates to a novel silane compound. The present invention also relates to a composition for forming an underlayer film between a substrate and a resist (for example, a photoresist, an electron beam resist, and an EUV resist) that are used in the production of semiconductor devices. More in detail, the present invention relates to a resist underlayer film forming composition for lithography for forming an underlayer film used for an underlayer of a photoresist in a lithography process of the production of semiconductor devices. In addition, the present invention relates to a forming method of a resist pattern using the underlayer film forming composition.

BACKGROUND ART

Conventionally, in the production of semiconductor devices, fine processing by lithography using a photoresist has been performed. The fine processing is a processing method for forming fine convexo-concave shapes corresponding to the following pattern on the surface of a substrate by: forming a thin film of a photoresist on a semiconductor substrate such as a silicon wafer; irradiating the resultant thin film with active rays such as ultraviolet rays through a mask pattern in which a pattern of a semiconductor device is depicted; developing the thin film; and subjecting the substrate to etching processing using the resultant photoresist pattern as a protecting film.

Recently, high integration of semiconductor devices has progressed and the adopted active rays tend to have a shorter wavelength, such as an ArF excimer laser (193 nm) and EUV light (13.5 nm), replacing a KrF excimer laser (248 nm). Following such a tendency, the influence of reflection of active rays on a semiconductor substrate has become a large issue.

Thus, in the production of semiconductor devices in recent years, for achieving various effects such as the reflection preventing effect, a resist underlayer film has become disposed between the semiconductor substrate and the photoresist.

For example, as an underlayer film between the semiconductor substrate and the photoresist, the use of a film known as a hardmask containing a metal element such as silicon (see, for example Patent Document 1) has been performed. In this case, the resist and the hardmask have components largely different from each other, so that the removal rates of the resist and the hardmask by dry etching largely depend on the type of a gas used for dry etching. By appropriately selecting the type of a gas, the hardmask can be removed by dry etching without a large decrease in the film thickness of the photoresist. Thus, the studies of a composition for a resist underlayer film have been performed; however, due to the diversity of characteristics required for the composition and so on, development of a novel material for the resist underlayer film is desired.

There is also a method for modifying the surface of the substrate from another viewpoint. For example, there is disclosed a method for changing the surface of the substrate after exposure to hydrophilic using a silane coupling agent having a sulfonyl group (see Patent Document 2).

A resist underlayer film containing silicon having a sulfonamide group is also disclosed (see Patent Documents 3 and 4).

PRIOR ART DOCUMENTS

Patent Documents

Patent Document 1: International Publication No. WO 2011/033965 pamphlet
Patent Document 2: Japanese Patent Application Publication No. 2005-112732 (JP 2005-112732 A)
Patent Document 3: Japanese Patent Application Publication No. 2009-244722 (JP 2009-244722 A)
Patent Document 4: International Publication No. WO 2011/033965 pamphlet

SUMMARY OF THE INVENTION

Problem to be Solved by the Invention

It is an object of the present invention to provide a resist underlayer film forming composition for lithography capable of performing fine processing of the substrate by utilizing a rectangular resist pattern and capable of being used in the production of semiconductor devices. More in detail, it is an object of the present invention to provide a resist underlayer film forming composition for lithography for forming a resist underlayer film capable of being used as a hardmask. In addition, it is an object of the present invention to provide a resist underlayer film forming composition for lithography for forming a resist underlayer film capable of being used as an anti-reflective coating. Furthermore, it is an object of the present invention to provide a resist underlayer film for lithography causing no intermixing with a resist and having a dry etching rate higher than that of the resist, and a resist underlayer film forming composition for forming the underlayer film. And then, it is an object of the present invention to provide a novel compound capable of being used for these resist underlayer film forming compositions for lithography.

Means for Solving the Problem

The present invention relates to, according to a first aspect, a silane compound of Formula (1-a) or Formula (1-b):

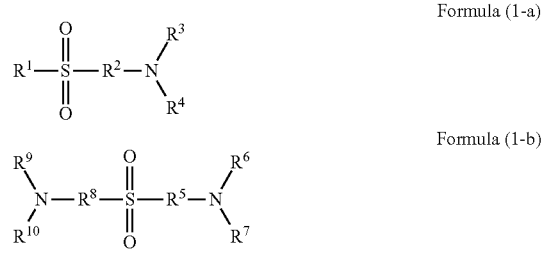

(in Formula (1-a), at least one group among $R^1$, $R^3$, and $R^4$ is a group in which a —Si(X)$_3$ group is bonded to a terminal of a $C_{1-10}$ alkylene group, and other group(s) among $R^1$, $R^3$, and $R^4$ is(are) a hydrogen atom, a $C_{1-10}$ alkyl group, or a $C_{6-40}$ aryl group; $R^2$ is a $C_{1-10}$ alkylene group or a $C_{6-40}$ arylene group; and X is an alkoxy group, an acyloxy group, or a halogen atom, in Formula (1-b), at least one group among $R^6$, $R^7$, $R^9$, and $R^{10}$ is a group in which a —Si(X)$_3$ group is bonded to a terminal of a $C_{1-10}$ alkylene group, and other group(s) among $R^6$, $R^7$, $R^9$, and $R^{10}$ is(are) a hydrogen atom, a $C_{1-10}$ alkyl group, or a $C_{6-40}$ aryl group; $R^5$ and $R^8$ are each a $C_{1-10}$ alkylene group or a $C_{6-40}$ arylene group; and X is an alkoxy group, an acyloxy group, or a halogen atom);

according to a second aspect, a resist underlayer film forming composition for lithography, comprising: as a silane, at least one among a hydrolyzable organosilane, a hydrolysis product thereof, and a hydrolysis-condensation product thereof, in which the silane includes the silane compound of Formula (1-a) or Formula (1-b) as described in the first aspect;

according to a third aspect, the resist underlayer film forming composition according to the second aspect, in which the silane compound of Formula (1-a) is a silane compound of Formula (2):

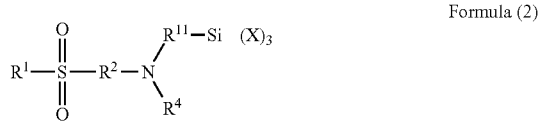

Formula (2)

(in Formula (2), $R^1$ and $R^4$ are each a hydrogen atom, a $C_{1-10}$ alkyl group, or a $C_{6-40}$ aryl group; $R^2$ is a $C_{1-10}$ alkylene group or a $C_{6-40}$ arylene group; $R^{11}$ is a $C_{1-10}$ alkylene group; and X is an alkoxy group, an acyloxy group, or a halogen atom);

according to a fourth aspect, the resist underlayer film forming composition for lithography according to the second or third aspect, in which the silane includes at least one among: a combination of at least one organic silicon compound selected from the group consisting of an organic silicon compound of Formula (3):

Formula (3)

(in Formula (3), $R^{21}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of these groups, and is bonded to a silicon atom through a Si—C bond; $R^{22}$ is an alkoxy group, an acyloxy group, or a halogen atom; and a is an integer of 0 to 3) and an organic silicon compound of Formula (4):

Formula (4)

(in Formula (4), $R^{31}$ is an alkyl group; $R^{32}$ is an alkoxy group, an acyloxy group, or a halogen atom; Y is an alkylene group or an arylene group; b is an integer of 0 or 1; and c is an integer of 0 or 1) with a silane compound of Formula (1-a) or Formula (1-b); a hydrolysis product thereof; and a hydrolysis-condensation product thereof;

according to a fifth aspect, the composition according to any one of the second aspect to the fourth aspect, in which at least one among a hydrolysis-condensation product of a silane compound of Formula (1-a) or Formula (1-b) and a hydrolysis-condensation product of a silane compound of Formula (1-a) or Formula (1-b) with an organic silicon compound of Formula (3) is contained as a polymer;

according to a sixth aspect, the composition according to any one of the second aspect to the fifth aspect, further comprising an acid;

according to a seventh aspect, the composition according to any one of the second aspect to the sixth aspect, further comprising water;

according to an eighth aspect, a resist underlayer film obtained by applying the resist underlayer film forming composition as described in any one of the second aspect to the seventh aspect onto a semiconductor substrate, and baking the composition;

according to a ninth aspect, a method for producing a semiconductor device, the method comprising: applying the resist underlayer film forming composition as described in any one of the second aspect to the seventh aspect onto a semiconductor substrate and baking the composition to form a resist underlayer film; applying a composition for a resist onto the resist underlayer film to form a resist film; exposing the resist film to light; developing the resist film after the exposing to obtain a patterned resist film; etching the resist underlayer film according to a pattern of the patterned resist film; and processing the semiconductor substrate according to a pattern of the resist film and the resist underlayer film; and according to a tenth aspect, a method for producing a semiconductor device, the method comprising: forming an organic underlayer film on a semiconductor substrate; applying the resist underlayer film forming composition as described in any one of the second aspect to the seventh aspect onto the organic underlayer film and baking the composition to form a resist underlayer film; applying a composition for a resist onto the resist underlayer film to form a resist film; exposing the resist film to light; developing the resist film after the exposing to obtain a patterned resist film; etching the resist underlayer film according to a pattern of the patterned resist film; etching the organic underlayer film according to a pattern of the pattered resist underlayer film; and processing the semiconductor substrate according to a pattern of the patterned organic underlayer film.

Effects of the Invention

In the resist underlayer film forming composition of the present invention, the silane compound of Formula (1-a) or Formula (1-b) has a sulfonyl group and an amino group, so that a resist underlayer film formed from the resist underlayer film forming composition can improve such a state that a cross-sectional shape of a patterned resist film becomes a footing shape.

In the resist underlayer film forming composition of the present invention, a silane compound of Formula (1-a) or Formula (1-b) can form a polyorganosiloxane structure by hydrolysis or partial hydrolysis of a hydrolyzable group of the silane compound, so that the resist underlayer film forming composition of the present invention can form a resist underlayer film capable of functioning as a hardmask or an anti-reflective coating in the production of semiconductor devices and hardly causing intermixing with a resist.

MODES FOR CARRYING OUT THE INVENTION

Figure 1:
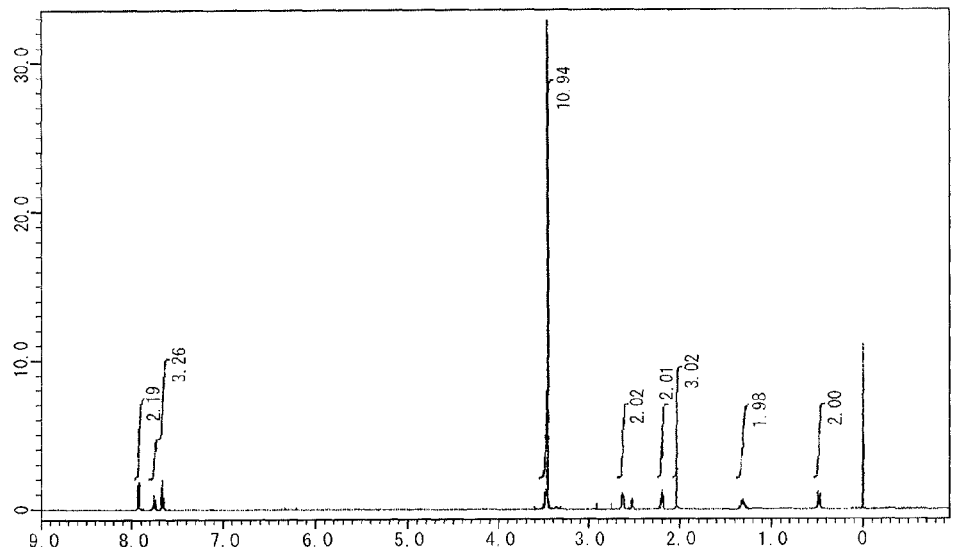
FIG. 1 is a graph showing an NMR spectrum of a compound (in which X is an ethoxy group) of Formula (1-1) obtained in Examples.
Figure 2:
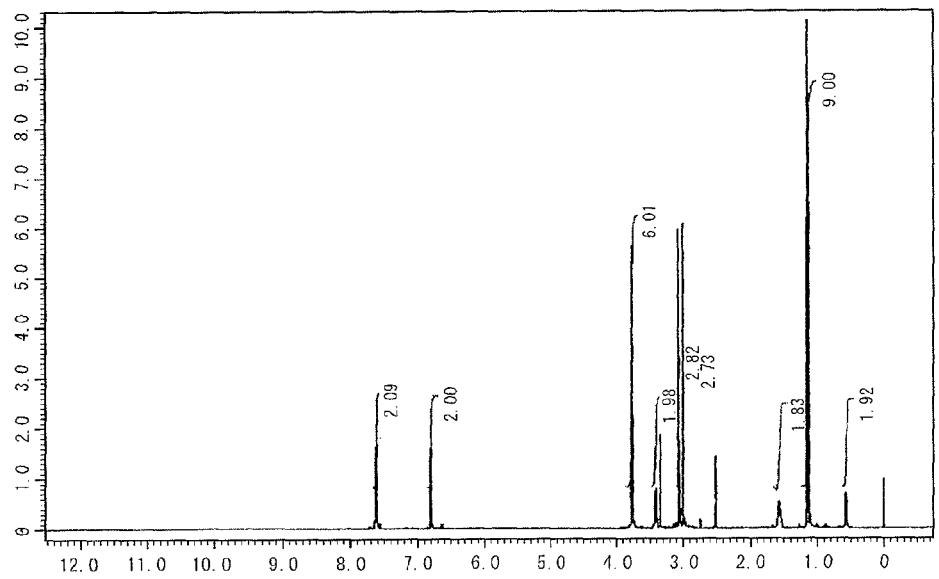
FIG. 2 is a graph showing an NMR spectrum of a compound (in which X is an ethoxy group) of Formula (1-2) obtained in Examples.

In the present invention, the resist underlayer film is formed by an applying method either on a substrate or on an organic underlayer film formed on a substrate and, on the resist underlayer film, a resist film (for example, a photoresist, an electron beam resist, and an EUV resist) is formed. Then, a resist pattern is formed by exposure and development, and either by dry etching the resist underlayer film according to the resist pattern to transfer the pattern, the substrate is processed according to the pattern, or by etching the organic underlayer film to transfer the pattern, the substrate is processed using the etched organic underlayer film.

In forming a fine pattern, for preventing a pattern collapse, the resist film thickness tends to become smaller. Due to the thinning of the resist, the dry etching for transferring the pattern to a film existing as an underlayer of the resist cannot be used to transfer the pattern unless the etching rate of the underlayer film is higher than that of the upper layer film. In the present invention, the substrate is coated in such an order that the substrate is coated with the resist underlayer film (containing an inorganic silicon-based compound) of the present specification either with or without an organic underlayer film interposed therebetween, and then the resist underlayer film is coated with a resist film (an organic resist film). An organic component film and an inorganic component film have dry etching rates largely different from each other depending on the selection of the etching gas. The dry etching rate of the organic component film is enhanced by an oxygen-based gas and the dry etching rate of the inorganic component film is enhanced by a halogen-containing gas.

For example, a resist pattern is formed and the pattern is transferred to the resist underlayer film of the present specification existing as an underlayer of the resist pattern by dry etching the resist underlayer film with a halogen-containing gas, and the substrate is processed with a halogen-containing gas according to the pattern which is transferred to the resist underlayer film. Alternatively, by dry etching the organic underlayer film existing as an underlayer of the resist underlayer film to which the pattern is transferred with an oxygen-based gas using the etched resist underlayer film, the pattern is transferred to the organic underlayer film, and the substrate is processed with a halogen-containing gas using the organic underlayer film to which the pattern is transferred.

In the present invention, the resist underlayer film functions as a hardmask, that is, a hydrolyzable group in the structures of Formula (1) and Formula (2) such as an alkoxy group, an acyloxy group, and a halogen atom is hydrolyzed or partially hydrolyzed to form a silanol group and then, by a condensation reaction of the silanol group, there is formed a polymer having a polyorganosiloxane structure which has a satisfactory function as a hardmask.

Then, the polyorganosiloxane structure (intermediate film) is effective as a hardmask for etching an organic underlayer film existing as an underlayer of the intermediate film or for processing (etching) the substrate. That is, the intermediate film has satisfactory dry etching resistance during the substrate processing or against an oxygen-based dry etching gas for etching the organic underlayer film.

The resist underlayer film of the present invention possesses enhancement of the dry etching rate of the resist underlayer film relative to the upper layer resist and dry etching resistance of the resist underlayer film during the substrate processing or the like.

The resist underlayer film formed from the resist underlayer film forming composition of the present invention contains a silane compound containing an organic group containing a sulfonyl group and a light absorbing group, a hydrolysis product thereof, or a hydrolysis-condensation product thereof, so that the shape of the resist pattern after exposure and development becomes a rectangular shape. Thus, fine processing of the substrate by a rectangular pattern becomes possible.

For example, the shape of the resist pattern formed by a resist underlayer film using a silane compound having a sulfonamide group which is described in the above patent documents becomes easily a shape having an inclination to a footing shape; however, the resist underlayer film of the present invention using a silane compound having a sulfone structure and an amino structure can improve the inclination of the shape of the resist pattern to a footing shape.

The present invention relates to a silane compound of Formula (1-a) or Formula (1-b).

Then, the present invention relates to a resist underlayer film forming composition for lithography containing as a silane, at least one among a hydrolyzable organosilane, a hydrolysis product thereof, and a hydrolysis-condensation product thereof in which the silane is a silane compound of Formula (1-a) or Formula (1-b).

The whole silane may contain a silane of Formula (1-a) or Formula (1-b) in a content of less than 50% by mole, for example 0.5 to 30% by mole, 0.5 to 25% by mole, 0.5 to 15% by mole, or 0.5 to 10% by mole.

The resist underlayer film forming composition of the present invention contains a hydrolyzable organosilane which is a silane compound of Formula (1-a) or Formula (1-b), a hydrolysis product thereof, or a hydrolysis-condensation product thereof, and a solvent. Then, the resist underlayer film forming composition of the present invention may contain as optional components, acids, water, alcohols, curing catalysts, acid generators, other organic polymers, light absorptive compounds, surfactants, and the like.

In the present invention, a silane compound of Formula (1-a) and a silane compound of Formula (1-b) can be used in combination, and the resist underlayer film forming composition of the present invention may contain one or two or more among a silane compound of Formula (1-a), a silane compound of Formula (1-b), a hydrolysis product of a silane compound of Formula (1-a), a hydrolysis product of a silane compound of Formula (1-b), a hydrolysis-condensation product of a silane compound of Formula (1-a), a hydrolysis-condensation product of a silane compound Formula (1-b), and a hydrolysis-condensation product of a silane compound of Formula (1-a) with a silane compound of Formula (1-b).

The solid content in the resist underlayer film forming composition of the present invention is, for example 0.1 to 50% by mass, or 0.1 to 30% by mass, 0.1 to 25% by mass. Here, the solid content is a component remaining after removing a solvent component from all components of the resist underlayer film forming composition.

The content of a hydrolyzable organosilane, a hydrolysis product thereof, or a hydrolysis-condensation product thereof in the solid content is 20% by mass or more, for example 50 to 100% by mass, 60 to 100% by mass, 70 to 100% by mass.

The hydrolyzable organosilane used in the present invention has a structure of Formula (1-a) or Formula (1-b).

Examples of the silane compound of Formula (1-a) include a silane compound of Formula (2).

In Formula (1), at least one group among $R^1$, $R^3$, and $R^4$ is a group in which a —Si(X)$_3$ group is bonded to a terminal of a $C_{1-10}$ alkylene group, and other group(s) among $R^1$, $R^3$, and $R^4$ is(are) a hydrogen atom, a $C_{1-10}$ alkyl group, or a $C_{6-40}$ aryl group; $R^2$ is a $C_{1-10}$ alkylene group or a $C_{6-40}$ arylene group; and X is an alkoxy group, an acyloxy group, or a halogen atom.

In Formula (2), at least one group among $R^6$, $R^7$, $R^9$, and $R^{10}$ is a group in which a —Si(X)$_3$ group is bonded to a terminal of a $C_{1-10}$ alkylene group, and other group(s) among $R^6$, $R^7$, $R^9$, and $R^{10}$ is(are) a hydrogen atom, a $C_{1-10}$ alkyl group, or a $C_{6-40}$ aryl group; $R^5$ and $R^8$ are each a $C_{1-10}$ alkylene group or a $C_{6-40}$ arylene group; and X is an alkoxy group, an acyloxy group, or a halogen atom.

Examples of the $C_{1-10}$ alkyl group include a methyl group, an ethyl group, an n-propyl group, an isopropyl group, a cyclopropyl group, an n-butyl group, an isobutyl group, a sec-butyl group, a tert-butyl group, a cyclobutyl group, a 1-methyl-cyclopropyl group, a 2-methyl-cyclopropyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-isopropyl-cyclopropyl group, a 2-isopropyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group. Among them, a methyl group, an ethyl group, and an n-propyl group are preferably used.

Examples of the $C_{1-10}$ alkylene group include alkylene groups corresponding to the above alkyl groups. And then, a methylene group, an ethylene group, and a propylene group are preferably used.

Examples of the $C_{6-40}$ aryl group include a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

Among them, a phenyl group is preferably used.

Examples of the $C_{6-40}$ arylene group include arylene groups corresponding to the above aryl groups. And then, a phenylene group is preferably used.

Examples of the hydrolyzable group in the hydrolyzable organosilane include an alkoxy group, an acyloxy group, and a halogen atom.

Examples of the alkoxy group include alkoxy groups having a linear, branched, or cyclic $C_{1-20}$ alkyl moiety such as a methoxy group, an ethoxy group, an n-propoxy group, an isopropoxy group, an n-butoxy group, an isobutoxy group, a sec-butoxy group, a tert-butoxy group, an n-pentyloxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, an n-hexyloxy group, a 1-methyl-n-pentyloxy group, a 2-methyl-n-pentyloxy group, and a 3-methyl-n-pentyloxy group.

Examples of the $C_{2-20}$ acyloxy group include a methylcarbonyloxy group, an ethylcarbonyloxy group, an n-propylcarbonyloxy group, an isopropylcarbonyloxy group, an n-butylcarbonyloxy group, an isobutylcarbonyloxy group, a sec-butylcarbonyloxy group, a tert-butylcarbonyloxy group, an n-pentylcarbonyloxy group, a 1-methyl-n-butylcarbonyloxy group, a 2-methyl-n-butylcarbonyloxy group, a 3-methyl-n-butylcarbonyloxy group, and a 1,1-dimethyl-n-propylcarbonyloxy group.

Examples of the halogen atom include a fluorine atom, a chlorine atom, a bromine atom, and an iodine atom.

The silane compound of Formula (1-a), the silane compound of Formula (1-b), and the silane compound (hydrolyzable organosilane) of Formula (2) can also be synthesized by allowing an amine compound to react with a sulfone compound.

Examples of the silane compound of Formula (1-a), the silane compound of Formula (1-b), and the silane compound (hydrolyzable organosilane) of Formula (2) include compounds of Formulae below. In Formulae below, X is the above alkoxy group, the above acyloxy group, or the above halogen atom.

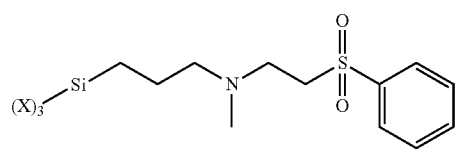

Formula (1-1)

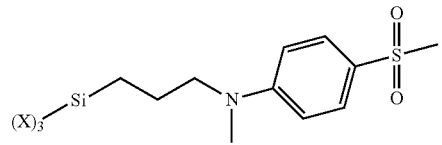

Formula (1-2)

Formula (1-3)
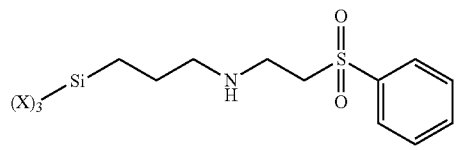
Formula (1-4)
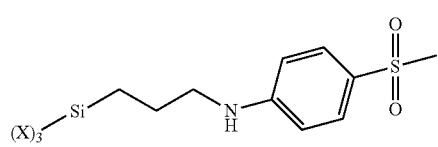
Formula (1-5)
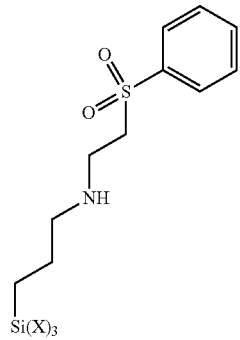
Formula (1-6)
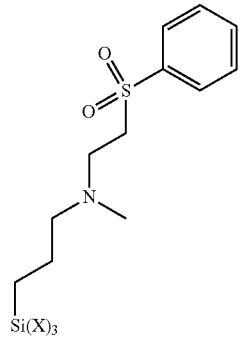
Formula (1-7)
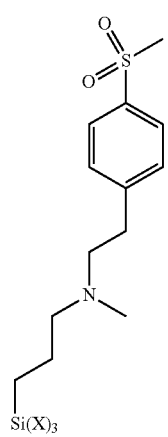
Formula (1-8)
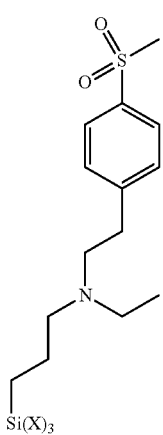
Formula (1-9)
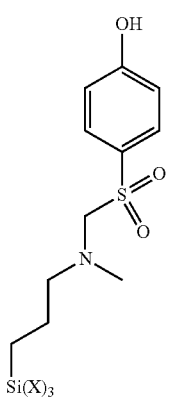
Formula (1-10)
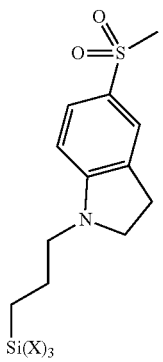
Formula (1-11)
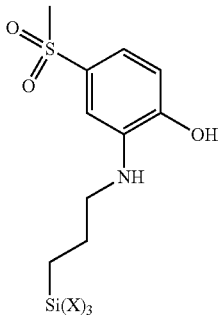

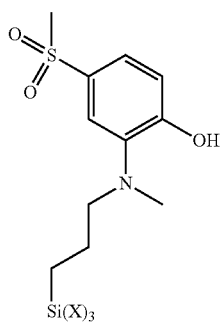
Formula (1-12)
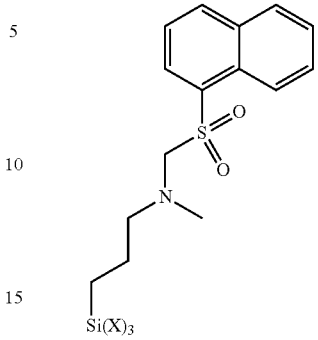
Formula (1-16)
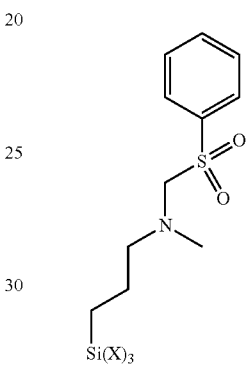
Formula (1-13)
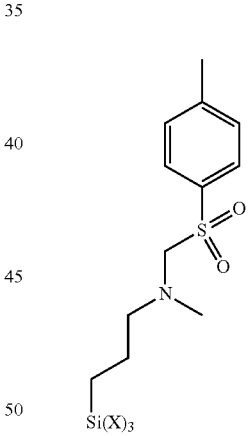
Formula (1-17)
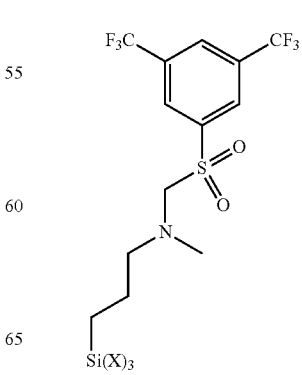
Formula (1-14)
Formula (1-18)
Formula (1-15)
Formula (1-19)

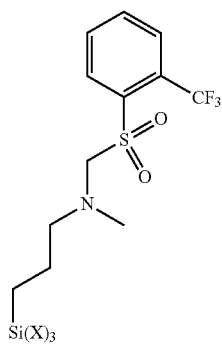
Formula (1-20)
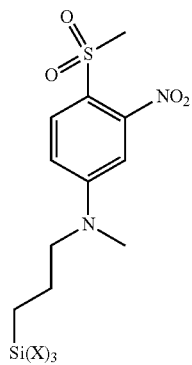
Formula (1-25)
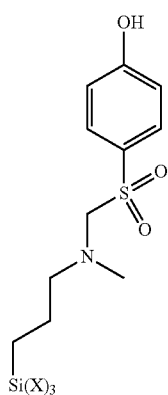
Formula (1-21)
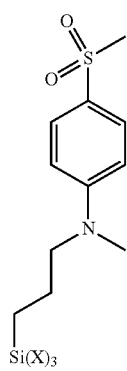
Formula (1-26)
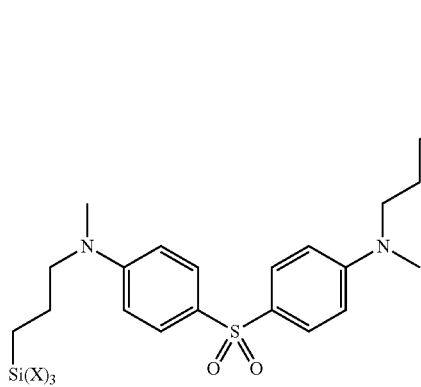
Formula (1-23)
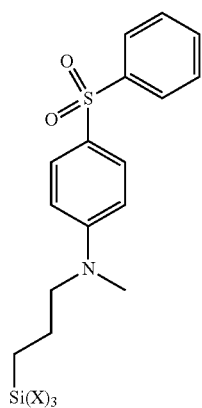
Formula (1-27)
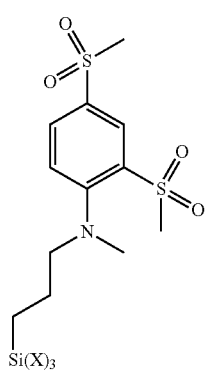
Formula (1-24)
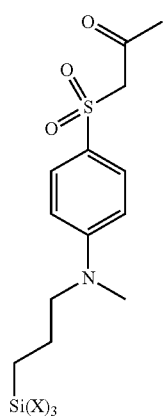
Formula (1-28)

Formula (1-29)
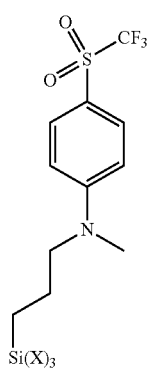
Formula (1-30)
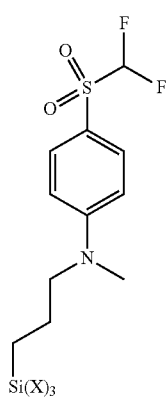
Formula (1-31)
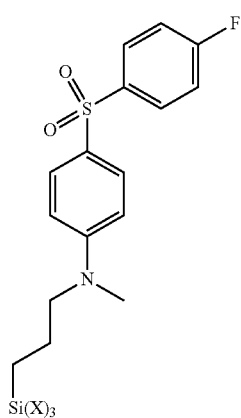
Formula (1-32)
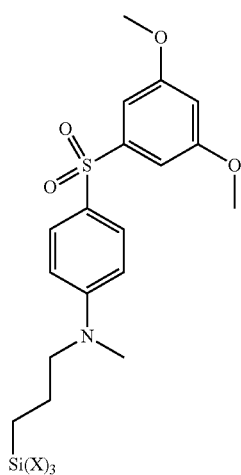
Formula (1-33)
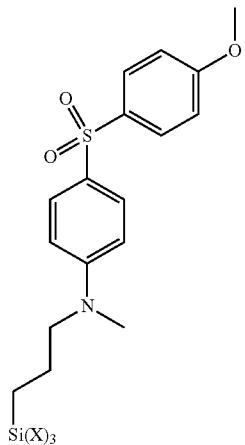
Formula (1-34)
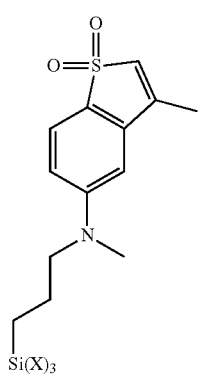
Formula (1-35)
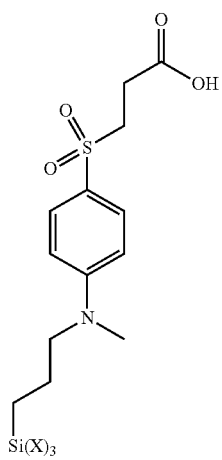

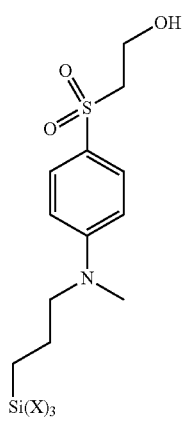
Formula (1-36)
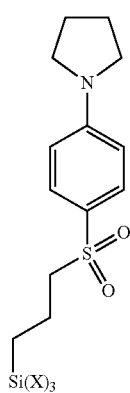
Formula (1-37)
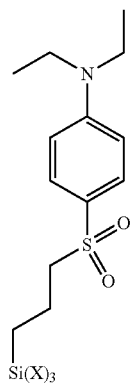
Formula (1-38)
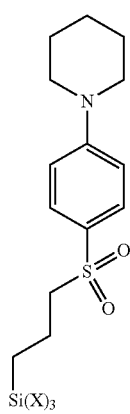
Formula (1-39)
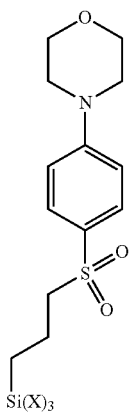
Formula (1-40)
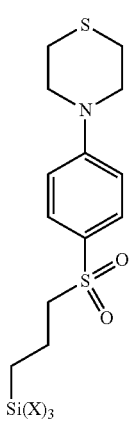
Formula (1-41)
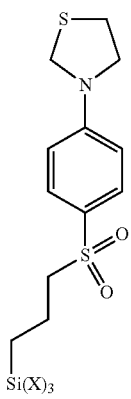
Formula (1-42)
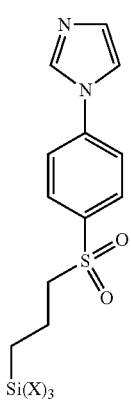
Formula (1-43)

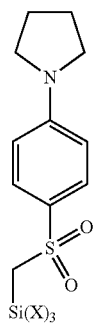 Formula (1-44)
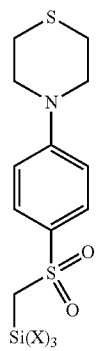 Formula (1-48)
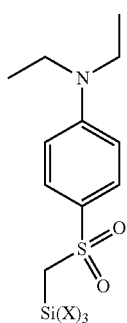 Formula (1-45)
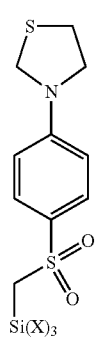 Formula (1-49)
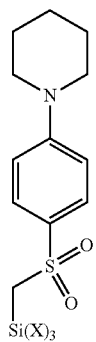 Formula (1-46)
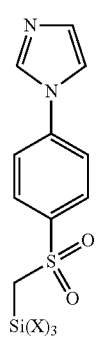 Formula (1-50)
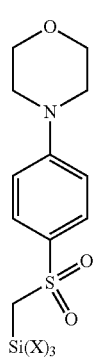 Formula (1-47)
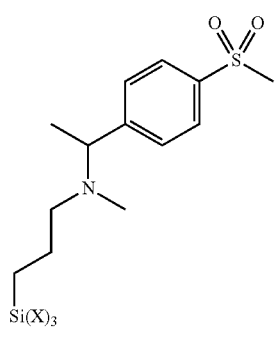 Formula (1-51)

-continued

Formula (1-52)

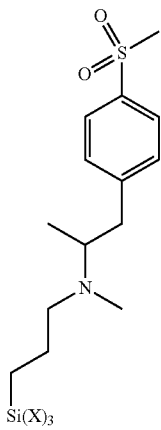

In the present invention, at least one among: a combination of at least one organic silicon compound selected from the group consisting of an organic silicon compound (hydrolyzable organosilane) of Formula (3) and an organic silicon compound (hydrolyzable organosilane) of Formula (4) with a silane compound (hydrolyzable organosilane) of Formula (1-a) or Formula (1-b); a hydrolysis product thereof; and a hydrolysis-condensation product thereof, can be contained.

In the present invention, at least one among a hydrolysis-condensation product of a silane compound (hydrolyzable organosilane) of Formula (1-a) or Formula (1-b) and a hydrolysis-condensation product of a silane compound (hydrolyzable organosilane) of Formula (1-a) or Formula (1-b) with an organic silicon compound (hydrolyzable organosilane) of Formula (3), can be used.

Further, in the present invention, a silane compound (hydrolyzable organosilane) of Formula (1-a) or Formula (1-b) and an organic silicon compound (hydrolyzable organosilane) of Formula (3) can be used in combination, and at least one among a silane compound (hydrolyzable organosilane) of Formula (1-a) or Formula (1-b), a hydrolysis product thereof, and a hydrolysis-condensation product thereof and at least one among an organic silicon compound of Formula (3), a hydrolysis product thereof, and a hydrolysis-condensation product thereof, can be used in combination.

In the resist underlayer film forming composition of the present invention, at least one among a silane compound of Formula (1-a), a silane compound of Formula (1-b), a hydrolysis product of a silane compound of Formula (1-a), a hydrolysis product of a silane compound of Formula (1-b), a hydrolysis-condensation product of a silane compound of Formula (1-a), a hydrolysis-condensation product of a silane compound of Formula (1-b), and a hydrolysis-condensation product of a silane compound of Formula (1-a) with a silane compound of Formula (1-b), and at least one among an organic silicon compound of Formula (3), a hydrolysis product thereof, a hydrolysis-condensation product thereof, a hydrolysis-condensation product of a silane compound of Formula (1-a) with an organic silicon compound of Formula (3), a hydrolysis-condensation product of a silane compound of Formula (1-b) with an organic silicon compound of Formula (3), and a hydrolysis-condensation product of a silane compound of Formula (1-a), a silane compound of Formula (1-b), and an organic silicon compound of Formula (3), can be used in combination.

The ratio between a silane compound (hydrolyzable organosilane) of Formula (1-a) or Formula (1-b) and an organic silicon compound of Formula (3) in a molar ratio can be used in a range of 1:0 to 1:200. In order to obtain a favorable resist shape, the ratio between a silane compound (hydrolyzable organosilane) of Formula (1-a) or Formula (1-b) and an organic silicon compound of Formula (3) in a molar ratio can be used in a range of 1:199 to 1:2.

These are preferably used as a hydrolysis-condensation product (polymer of polyorganosiloxane), and a hydrolysis-condensation product (polymer of polyorganosiloxane) of a silane compound (hydrolyzable organosilane) of Formula (1-a) or Formula (1-b) with an organic silicon compound (hydrolyzable organosilane) of Formula (3) is preferably used.

In the organic silicon compound (hydrolyzable organosilane) of Formula (3), $R^1$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination thereof, and is bonded to a silicon atom through a Si—C bond; $R^2$ is an alkoxy group, an acyloxy group, or a halogen atom; and a is an integer of 0 to 3.

Examples of an alkyl group, an aryl group, an aralkyl group, a halogenated alkyl group, a halogenated aryl group, a halogenated aralkyl group, an alkenyl group, and an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, and further an alkoxy group, an acyloxy group, and a halogen atom contained in a hydrolyzable group of $R^1$ and $R^2$, include examples thereof described above with respect to Formula (1-a) and Formula (1-b).

Examples of the organic silicon compound (hydrolyzable organosilane) of Formula (3) include tetramethoxysilane, tetrachlorosilane, tetraacetoxysilane, tetraethoxysilane, tetra-n-propoxysilane, tetraisopropoxysilane, tetra-n-butoxysilane, tetraacetoxysilane, methyltrimethoxysilane, methyltriethoxysilane, methyltrichlorosilane, methyltriacetoxysilane, methyltripropoxysilane, methyltriacetoxysilane, methyltributoxysilane, methyltripropoxysilane, methyltriamyloxysilane, methyltriphenoxysilane, methyltribenzyloxysilane, methyltriphenethyloxysilane, glycidoxymethyltrimethoxysilane, glycidoxymethyltriethoxysilane, α-glycidoxyethyltrimethoxysilane, α-glycidoxyethyltriethoxysilane, β-glycidoxyethyltrimethoxysilane, β-glycidoxyethyltriethoxysilane, α-glycidoxypropyltrimethoxysilane, α-glycidoxypropyltriethoxysilane, β-gycidoxypropytrimethoxysilane, β-glycidoxypropyltriethoxysilane, γ-glycidoxypropyltrimethoxysilane, γ-glycidoxypropyltriethoxysilane, γ-glycidoxypropyltripropoxysilane, γ-glycidoxypropyltributoxysilane, γ-glycidoxypropyltriphenoxysilane, α-gycidoxybutyltrimethoxysilane, α-glycidoxybutyltriethoxysilane, β-gycidoxybutyltriethoxysilane, γ-glycidoxybutyltrimethoxysilane, γ-glycidoxybutyltriethoxysilane, δ-glycidoxybutyltrimethoxysilane, δ-glycidoxybutyltriethoxysilane, (3,4-epoxycyclohexyl)methyltrimethoxysilane, (3,4-epoxycyclohexyl)methyltriethoxysilane, β-(3,4-epoxycyclohexyl)ethyltrimethoxysilane, β-(3,4-epoxycyclohexyl)ethyltriethoxysilane, β-(3,4-epoxycyclohexyl)ethyltripropoxysilane, β-(3,4-epoxycyclohexyl)ethyltributoxysilane, β-(3,4- epoxycyclohexyl)ethyltriphenoxysilane, γ-(3,4-epoxycyclohexyl)propyltrimethoxysilane, γ-(3,4-epoxycyclohexyl)propyltriethoxysilane, δ-(3,4-epoxycyclohexyl)butyltrimethoxysilane, δ-(3,4-epoxycyclohexyl)butyltriethoxysilane, glycidoxymethylmethyldimethoxysilane, glycidoxymethylmethyldiethoxysilane, α-glycidoxyethylmethyldimethoxysilane, α-glycidoxyethylmethyldiethoxysilane, β-glycidoxyethylmethyldimethoxysilane, β-glycidoxyethylethyldimethoxysilane, α-glycidoxypropylmethyldimethoxysilane, α-gycidoxypropylmethyldiethoxysilane, β-glycidoxypropylmethyldimethoxysilane, β-gycidoxypropylethyldimethoxysilane, γ-glycidoxypropylmethyldimethoxysilane, γ-glycidoxypropylmethyldiethoxysilane, γ-glycidoxypropylmethyldipropoxysilane, γ-glycidoxypropylmethyldibutoxysilane, γ-glycidoxypropylmethyldiphenoxysilane, γ-glycidoxypropylethyldimethoxysilane, γ-glycidoxypropylethyldiethoxysilane, γ-glycidoxypropylvinyldimethoxysilane, γ-glycidoxypropylvinyldiethoxysilane, ethyltrimethoxysilane, ethyltriethoxysilane, vinyltrimethoxysilane, vinyltrichlorosilane, vinyltriacetoxysilane, vinyltriethoxysilane, vinyltriacetoxysilane, phenyltrimethoxysilane, phenyltrichlorosilane, phenyltriacetoxysilane, phenyltriethoxysilane, phenyltriacetoxysilane, γ-chloropropyltrimethoxysilane, γ-chloropropyltriethoxysilane, γ-chloropropyltriacetoxysilane, 3,3,3-trifluoropropyltrimethoxysilane, γ-methacryloxypropyltrimethoxysilane, γ-mercaptopropyltrimethoxysilane, γ-mercaptopropyltriethoxysilane, β-cyanoethyltriethoxysilane, chloromethyltrimethoxysilane, chloromethyltriethoxysilane, dimethyldimethoxysilane, phenylmethyldimethoxysilane, dimethyldiethoxysilane, phenylmethyldiethoxysilane, γ-chloropropylmethyldimethoxysilane, γ-chloropropylmethyldiethoxysilane, dimethyldiacetoxysilane, γ-methacryloxypropylmethyldimethoxysilane, γ-methacryloxypropylmethyldiethoxysilane, γ-mercaptopropylmethyldimethoxysilane, γ-mercaptomethyldiethoxysilane, methylvinyldimethoxysilane, methylvinyldiethoxysilane, phenylsulfonylaminopropyltriethoxysilane, methylsulfonylaminopropyltriethoxysilane, phenylsulfonylaminopropyltrimethoxysilane, and methylsulfonylaminopropyltrimethoxysilane.

Particularly preferred is a combination of a tetraalkoxysilane such as tetramethoxysilane and tetraethoxysilane with a phenyltrialkoxysilane such as phenyltrimethoxysilane and phenyltriethoxysilane. Further preferred is a combination of the above combination with an alkyltrialkoxysilane such as methyltrimethoxysilane and methyltriethoxysilane.

Examples of the organic silicon compound (hydrolyzable organosilane) of Formula (3) include compounds having structures of Formulae below. $R^{22}$ in the structures is the same as defined as $R^{22}$ in Formula (3).

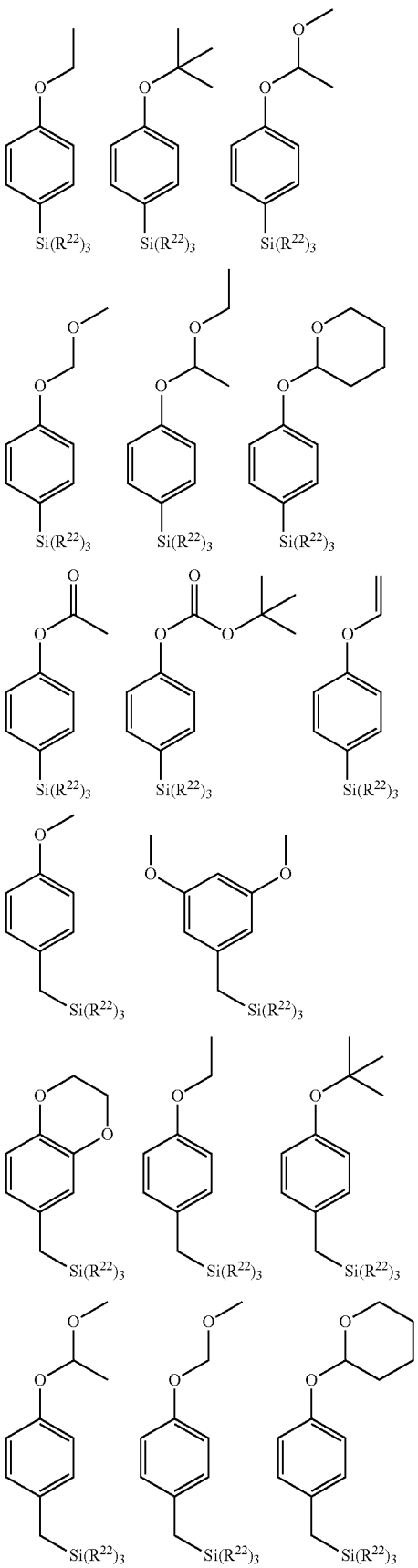

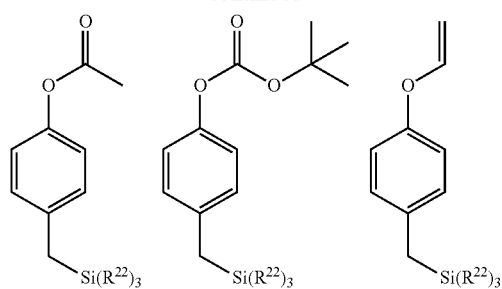
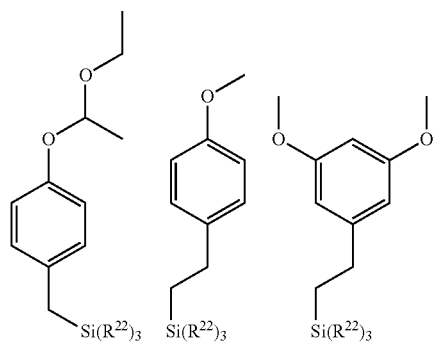
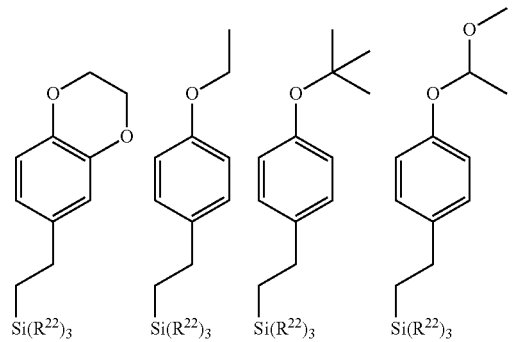
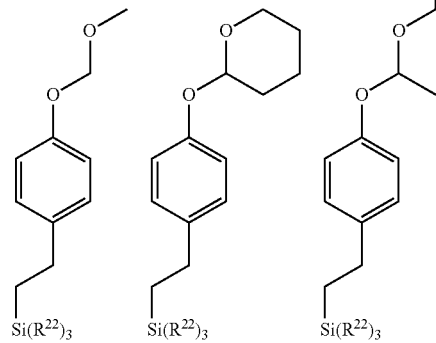
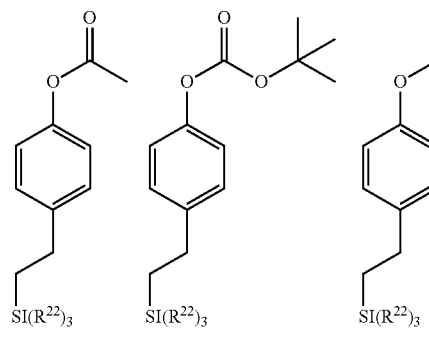
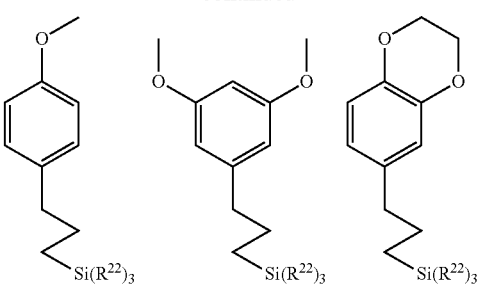
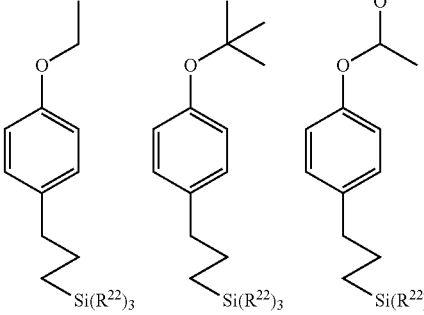
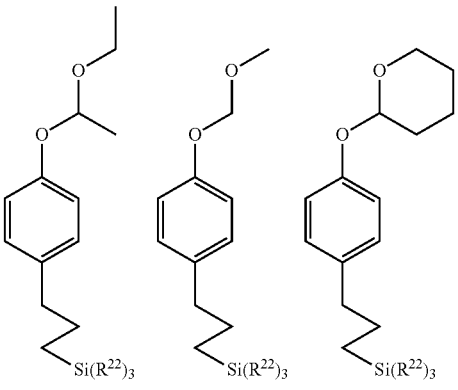
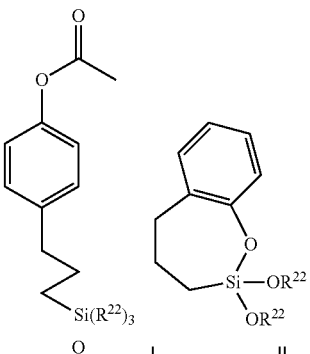
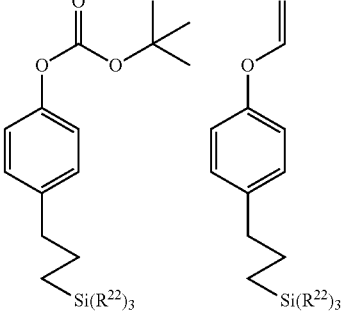

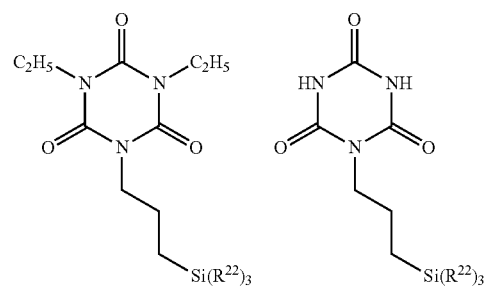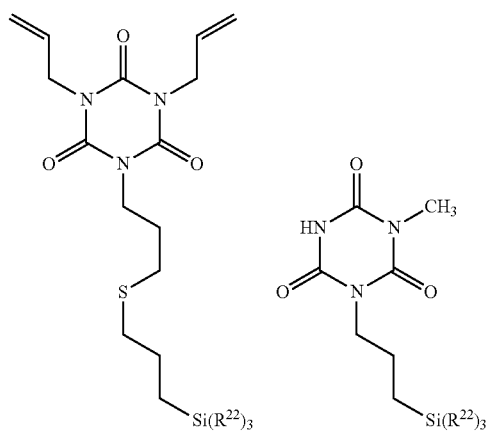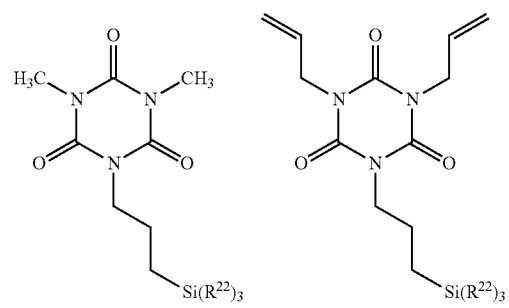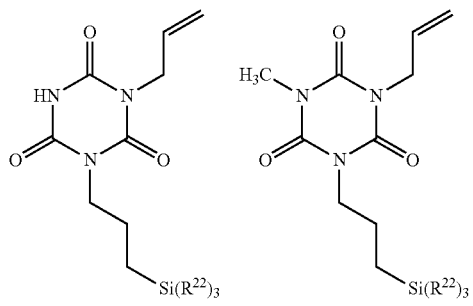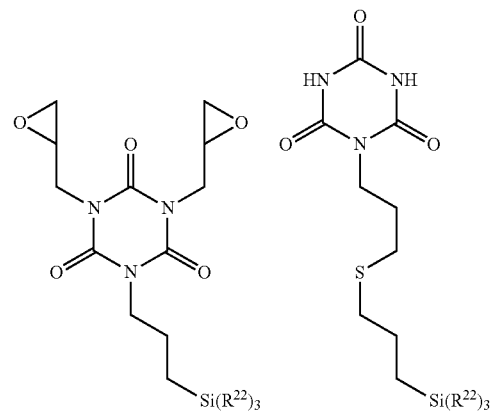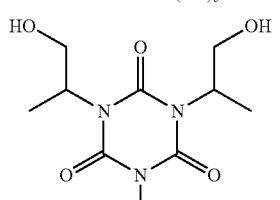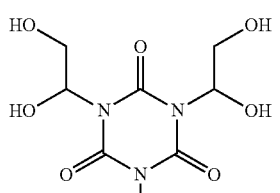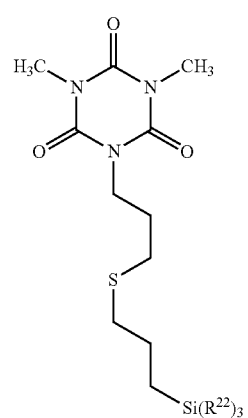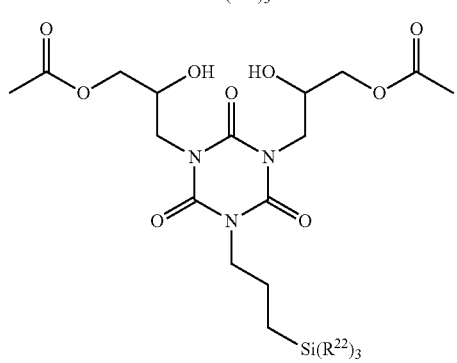

-continued

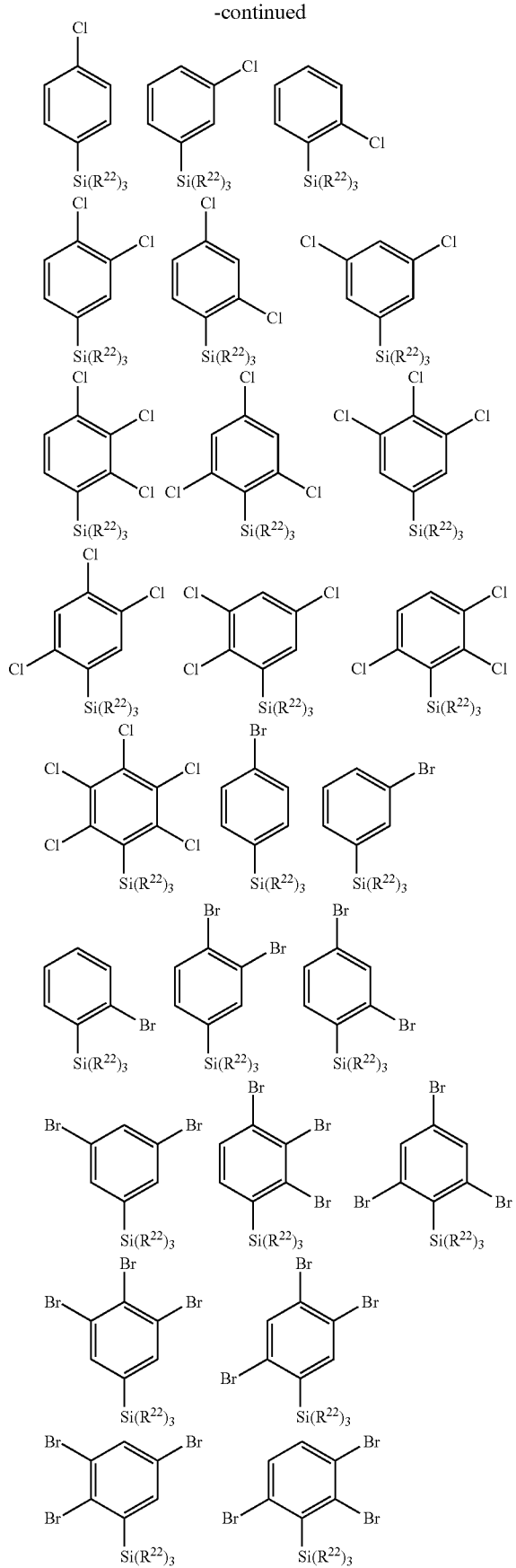

-continued

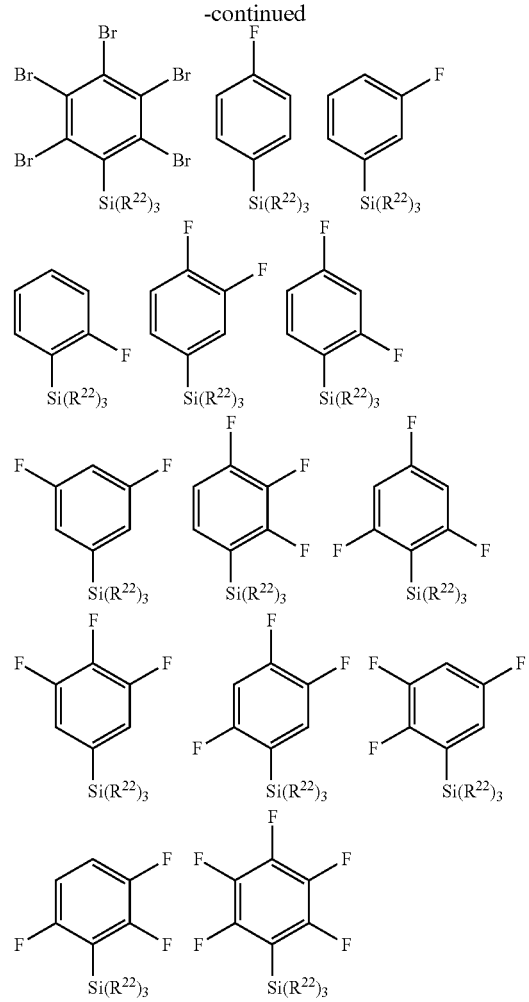

In the organic silicon compound (hydrolyzable organosilane) of Formula (4), $R^{31}$ is an alkyl group; $R^{32}$ is an alkoxy group, an acyloxy group, or a halogen atom; Y is an alkylene group or an arylene group; b is an integer of 0 or 1; and c is an integer of 0 or 1.

As the alkyl group, the alkoxy group, the acyloxy group, or the halogen atom, those exemplified above with respect to Formula (1-a) and Formula (1-b) can be used. Examples of the alkylene group and the arylene group include divalent organic groups corresponding to the above examples of the alkyl group and the above examples of the aryl group, respectively.

Examples of the organic silicon compound (hydrolyzable organosilane) of Formula (4) include methylenebis(trimethoxysilane), methylenebis(trichlorosilane), methylenebis(triacetoxysilane), ethylenebis(triethoxysilane), ethylenebis(trichlorosilane), ethylenebis(triacetoxysilane), propylenebis(triethoxysilane), butylenebis(trimethoxysilane), phenylenebis(trimethoxysilane), phenylenebis(triethoxysilane), phenylenebis(methyldiethoxysilane), phenylenebis(methyldimethoxysilane), naphthylenebis(trimethoxysilane), bis(trimethoxydisilane), bis(triethoxydisilane), bis(ethyldiethoxydisilane), and bis(methyldimethoxydisilane).

Specific examples of the hydrolysis-condensation product of a silane compound (hydrolyzable organosilane) of Formula (1-a) or Formula (1-b) with an organic silicon compound (hydrolyzable organosilane) of Formula (3) include compounds of Formulae (A-1) to (A-4) below.

Formula (A-1)
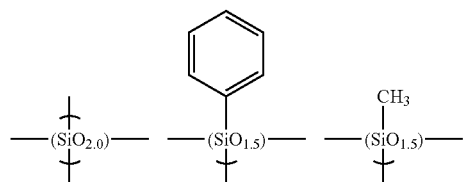

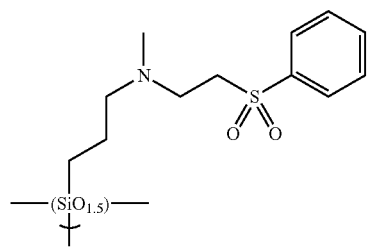

Formula (A-2)
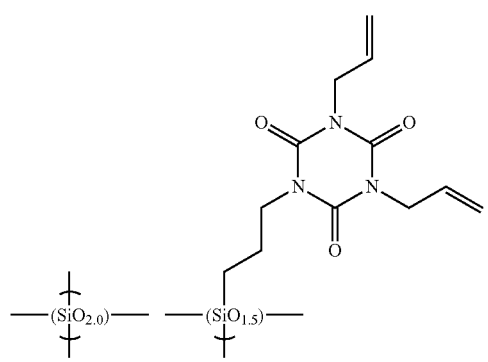

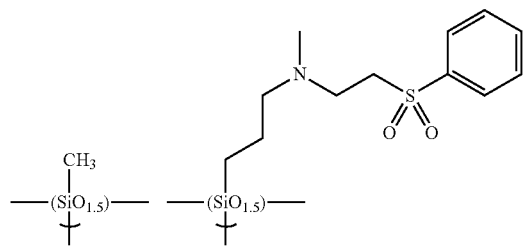

Formula (A-3)
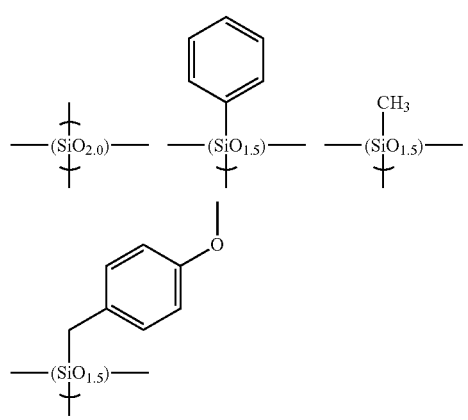

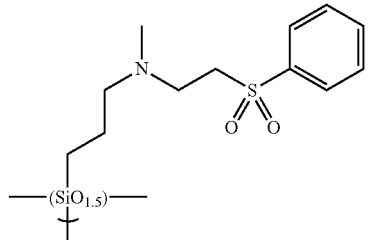

Formula (A-4)
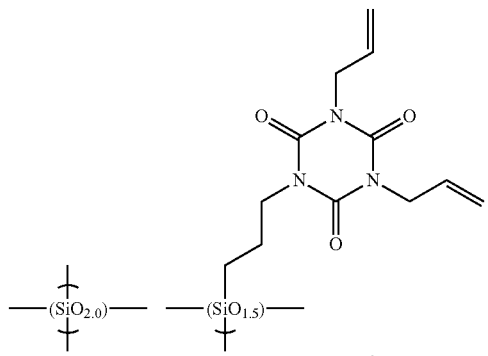

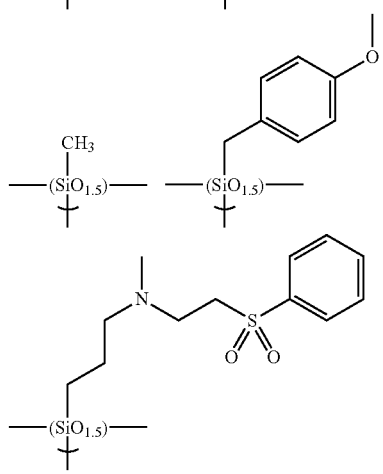

As the hydrolysis-condensation product (polyorganosiloxane) of a silane compound (hydrolyzable organosilane) of Formula (1-a) or Formula (1-b) or the hydrolysis-condensation product (polyorganosiloxane) of a silane compound (hydrolyzable organosilane) of Formula (1-a) or Formula (1-b) with at least one among an organic silicon compound of Formula (3) and an organic silicon compound of Formula (4), a condensation product having a weight average molecular weight of 1,000 to 1,000,000 or 1,000 to 100,000 can be obtained. This molecular weight is a molecular weight obtained by a GPC analysis in terms of polystyrene.

Examples of the conditions for the GPC measurement include: using a GPC apparatus (trade name: HLC-8220GPC; manufactured by Tosoh Corporation); using a GPC column (trade names: Shodex KF803L, KF802, and KF801; manufactured by Showa Denko K.K.); using a column temperature of 40° C.; using tetrahydrofuran as the eluting liquid (eluting solvent); using a flow amount (flow rate) of 1.0 mL/min; and using polystyrene (manufactured by Showa Denko K.K.) as the standard sample.

For the hydrolysis of an alkoxysilyl group, an acyloxysilyl group, or a halogenated silyl group, water is used in an amount of 0.5 to 100 mol, preferably 1 to 10 mol, relative to 1 mol of a hydrolyzable group.

A catalyst for the hydrolysis can be used in an amount of 0.001 to 10 mol, preferably 0.001 to 1 mol, relative to 1 mol of a hydrolyzable group.

The reaction temperature for performing the hydrolysis and the condensation is usually 20 to 80° C.

The hydrolysis may be performed either perfectly or partially. That is, in the hydrolysis-condensation product thereof, a hydrolysis product or a monomer may remain.

During the hydrolysis and the condensation, a catalyst can be used.

Examples of the catalyst for the hydrolysis include metal chelate compounds, organic acids, inorganic acids, organic bases, and inorganic bases.

Examples of the metal chelate compound as the catalyst for the hydrolysis include: titanium chelate compounds such as triethoxy-mono(acetylacetonate)titanium, tri-n-propoxy-mono(acetylacetonate)titanium, triisopropoxy-mono(acetylacetonate)titanium, tri-n-butoxy-mono(acetylacetonate)titanium, tri-sec-butoxy-mono(acetylacetonate)titanium, tri-tert-butoxy-mono(acetylacetonate)titanium, diethoxy-bis(acetylacetonate)titanium, di-n-propoxy-bis(acetylacetonate)titanium, di-isopropoxy-bis(acetylacetonate)titanium, di-n-butoxy-bis(acetylacetonate)titanium, di-sec-butoxy-bis(acetylacetonate)titanium, di-tert-butoxy-bis(acetylacetonate)titanium, monoethoxy-tris(acetylacetonate)titanium, mono-n-propoxy-tris(acetylacetonate)titanium, mono-isopropoxy-tris(acetylacetonate)titanium, mono-n-butoxy-tris(acetylacetonate)titanium, mono-sec-butoxy-tris(acetylacetonate)titanium, mono-tert-butoxy-tris(acetylacetonate)titanium, tetrakis(acetylacetonate)titanium, triethoxy-mono(ethylacetoacetate)titanium, tri-n-propoxy-mono(ethylacetoacetate)titanium, tri-isopropoxy-mono(ethylacetoacetate)titanium, tri-n-butoxy-mono(ethylacetoacetate)titanium, tri-sec-butoxy-mono(ethylacetoacetate)titanium, tri-tert-butoxy-mono(ethylacetoacetate)titanium, diethoxy-bis(ethylacetoacetate)titanium, di-n-propoxy-bis(ethylacetoacetate)titanium, di-isopropoxy-bis(ethylacetoacetate)titanium, di-n-butoxy-bis(ethylacetoacetate)titanium, di-sec-butoxy-bis(ethylacetoacetate)titanium, di-tert-butoxy-bis(ethylacetoacetate)titanium, monoethoxy-tris(ethylacetoacetate)titanium, mono-n-propoxy-tris(ethylacetoacetate)titanium, mono-isopropoxy-tris(ethylacetoacetate)titanium, mono-n-butoxy-tris(ethylacetoacetate)titanium, mono-sec-butoxy-tris(ethylacetoacetate)titanium, mono-tert-butoxy-tris(ethylacetoacetate)titanium, tetrakis(ethylacetoacetate)titanium, mono(acetylacetonate)tris(ethylacetoacetate)titanium, bis(acetylacetonate)bis(ethylacetoacetate)titanium, and tris(acetylacetonate)mono(ethylacetoacetate)titanium; zirconium chelate compounds such as triethoxy-mono(acetylacetonate)zirconium, tri-n-propoxy-mono(acetylacetonate)zirconium, tri-isopropoxy-mono(acetylacetonate)zirconium, tri-n-butoxy-mono(acetylacetonate)zirconium, tri-sec-butoxy-mono(acetylacetonate)zirconium, tri-tert-butoxy-mono(acetylacetonate)zirconium, diethoxy-bis(acetylacetonate)zirconium, di-n-propoxy-bis(acetylacetonate)zirconium, di-isopropoxy-bis(acetylacetonate)zirconium, di-n-butoxy-bis(acetylacetonate)zirconium, di-sec-butoxy-bis(acetylacetonate)zirconium, di-tert-butoxy-bis(acetylacetonate)zirconium, monoethoxy-tris(acetylacetonate)zirconium, mono-n-propoxy-tris(acetylacetonate)zirconium, mono-isopropoxy-tris(acetylacetonate)zirconium, mono-n-butoxy-tris(acetylacetonate)zirconium, mono-sec-butoxy-tris(acetylacetonate)zirconium, mono-tert-butoxy-tris(acetylacetonate)zirconium, tetrakis(acetylacetonate)zirconium, triethoxy-mono(ethylacetoacetate)zirconium, tri-n-propoxy-mono(ethylacetoacetate)zirconium, tri-isopropoxy-mono(ethylacetoacetate)zirconium, tri-n-butoxy-mono(ethylacetoacetate)zirconium, tri-sec-butoxy-mono(ethylacetoacetate)zirconium, tri-tert-butoxy-mono(ethylacetoacetate)zirconium, diethoxy-bis(ethylacetoacetate)zirconium, di-n-propoxy-bis(ethylacetoacetate)zirconium, di-isopropoxy-bis(ethylacetoacetate)zirconium, di-n-butoxy-bis(ethylacetoacetate)zirconium, di-sec-butoxy-bis(ethylacetoacetate)zirconium, di-tert-butoxy-bis(ethylacetoacetate)zirconium, monoethoxy-tris(ethylacetoacetate)zirconium, mono-n-propoxy-tris(ethylacetoacetate)zirconium, mono-isopropoxy-tris(ethylacetoacetate)zirconium, mono-n-butoxy-tris(ethylacetoacetate)zirconium, mono-sec-butoxy-tris(ethylacetoacetate)zirconium, mono-tert-butoxy-tris(ethylacetoacetate)zirconium, tetrakis(ethylacetoacetate)zirconium, mono(acetylacetonate)tris(ethylacetoacetate)zirconium, bis(acetylacetonate)bis(ethylacetoacetate)zirconium, and tris(acetylacetonate)mono(ethylacetoacetate)zirconium; and aluminum chelate compounds such as tris(acetylacetonate)aluminum and tris(ethylacetoacetate)aluminum.

Examples of the organic acid as the catalyst for the hydrolysis include acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, and tartaric acid.

Examples of the inorganic acid as the catalyst for the hydrolysis include hydrochloric acid, nitric acid, sulfuric acid, hydrofluoric acid, and phosphoric acid.

Examples of the organic base as the catalyst for the hydrolysis include pyridine, pyrrole, piperazine, pyrrolidine, piperidine, picoline, trimethylamine, triethylamine, monoethanolamine, diethanolamine, dimethylmonoethanolamine, monomethyldiethanolamine, triethanolamine, diazabicyclo octane, diazabicyclo nonane, diazabicyclo undecene, and tetramethylammonium hydroxide. Examples of the inorganic base as the catalyst for the hydrolysis include ammonia, sodium hydroxide, potassium hydroxide, barium hydroxide, and calcium hydroxide. Among these catalysts, metal chelate compounds, organic acids, and inorganic acids are preferred and these catalysts may be used individually or in combination of two or more thereof.

Examples of the organic solvent used for the hydrolysis include: aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; aromatic hydrocarbon solvents such as benzene, toluene, xylene, ethylbenzene, trimethylbenzene, methylethylbenzene, n-propylbenzene, isopropylbenzene, diethylbenzene, isobutylbenzene, triethylbenzene, di-isopropylbenzene, n-amylnaphthalene, and trimethylbenzene; monoalcohol solvents such as methanol, ethanol, n-propanol, isopropanol, n-butanol, isobutanol, sec-butanol, tert-butanol, n-pentanol, isopentanol, 2-methylbutanol, sec-pentanol, tert-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenylmethylcarbinol, diacetone alcohol, and cresol; polyalcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerin; ketone solvents such as acetone, methyl ethyl ketone, methyl-n-propyl ketone, methyl-n-butyl ketone, diethyl ketone, methyl-isobutyl ketone, methyl-n-pentyl ketone, ethyl-n-butyl ketone, methyl-n-hexyl ketone, di-isobutyl ketone, trimethylnonanone, cyclohexanone, methylcyclohexanone, 2,4-pentanedione, acetonylacetone, diacetone alcohol, acetophenone, and fenchone; ether solvents such as ethyl ether, isopropyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethyleneglycol monomethyl ether acetate, ethyleneglycol monoethyl ether acetate, diethyleneglycol monomethyl ether acetate, diethyleneglycol monoethyl ether acetate, diethyleneglycol mono-n-butyl ether acetate, propyleneglycol monomethyl ether acetate, propyleneglycol monoethyl ether acetate, propyleneglycol monopropyl ether acetate, propyleneglycol monobutyl ether acetate, dipropyleneglycol monomethyl ether acetate, dipropyleneglycol monoethyl ether acetate, glycol diacetate, methoxytriglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethyl sulfoxide, sulfolane, and 1,3-propane sultone. These solvents may be used individually or in combination of two or more thereof.

Particularly preferred are ketone solvents such as acetone, methyl ethyl ketone, methyl-n-propyl ketone, methyl-n-butyl ketone, diethyl ketone, methyl-isobutyl ketone, methyl-n-pentyl ketone, ethyl-n-butyl ketone, methyl-n-hexyl ketone, di-isobutyl ketone, trimethylnonanone, cyclohexanone, methylcyclohexanone, 2,4-pentanedione, acetonylacetone, diacetone alcohol, acetophenone, and fenchone (1,1,3-trimethyl-2-norbornene) regarding the preservation stability of the solution.

From the hydrolysis-condensation product (polymer) obtained by hydrolyzing and condensing a hydrolyzable organosilane in a solvent using a catalyst, an alcohol as a by-product, the used catalyst for the hydrolysis, and the used water can be simultaneously removed by distilling them under reduced pressure or the like. An acid catalyst or a base catalyst used for the hydrolysis can be removed by neutralization or ion exchange. Then, with respect to the resist underlayer film forming composition for lithography of the present invention, in the resist underlayer film forming composition containing the hydrolysis-condensation product thereof, an acid (for example, organic acid), water, an alcohol, or a combination thereof can be blended to stabilize the composition.

Examples of the organic acid include oxalic acid, malonic acid, methylmalonic acid, succinic acid, maleic acid, malic acid, tartaric acid, phthalic acid, citric acid, glutaric acid, citric acid, lactic acid, and salicylic acid. Among them, oxalic acid and maleic acid are preferred. The amount of the organic acid to be blended in the composition is 0.5 to 5.0 parts by mass, relative to 100 parts by mass of the condensation product (polyorganosiloxane). As the water to be blended in the composition, pure water, ultrapure water, ion-exchanged water, or the like can be used and the blending amount thereof can be 1 to 20 parts by mass, relative to 100 parts by mass of the resist underlayer film forming composition.

The alcohol to be blended in the composition is preferably an alcohol that can be easily diffused by heating the composition after the application of the composition, and examples thereof include methanol, ethanol, propanol, isopropanol, and butanol. The blending amount of the alcohol can be 1 to 20 parts by mass, relative to 100 parts by mass of the resist underlayer film forming composition.

As an additive, bisphenol S or a bisphenol S derivative can be blended in the composition. The blending amount of bisphenol S or a bisphenol S derivative is 0.01 to 20 parts by mass, or 0.01 to 10 parts by mass, or 0.01 to 5 parts by mass, relative to 100 parts by mass of the polyorganosiloxane.

Preferred examples of bisphenol S or a bisphenol S derivative include the compounds below.

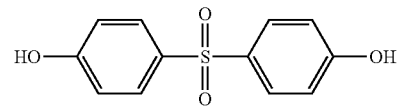

Formula (C-1)

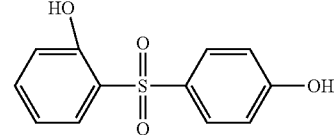

Formula (C-2)

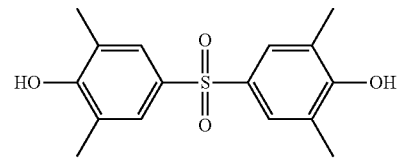

Formula (C-3)

Formula (C-4)
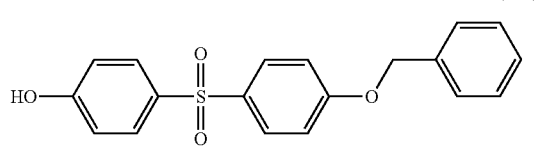
Formula (C-5)
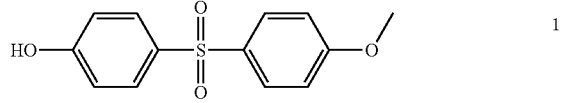
Formula (C-6)
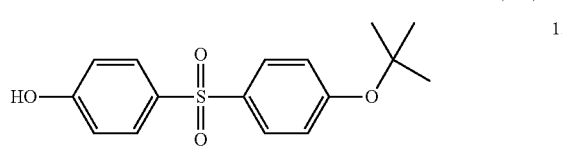
Formula (C-7)
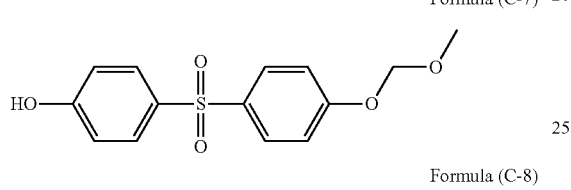
Formula (C-8)
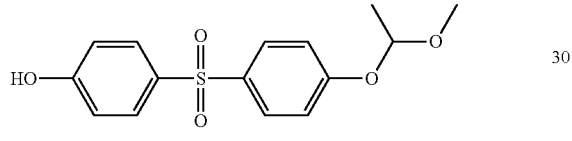
Formula (C-9)
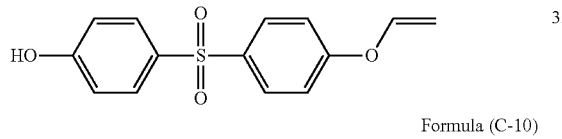
Formula (C-10)
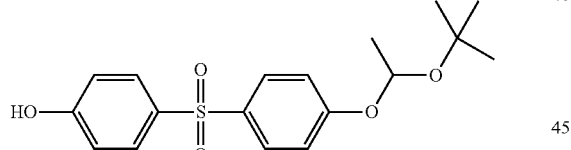
Formula (C-11)
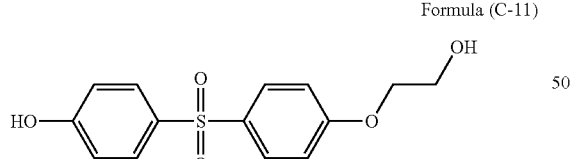
Formula (C-12)
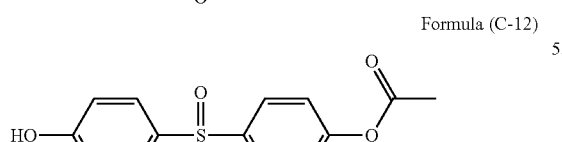
Formula (C-13)
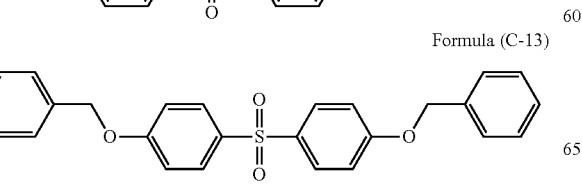
Formula (C-14)
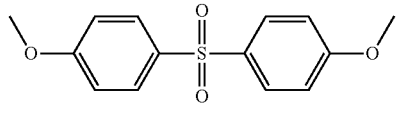
Formula (C-15)
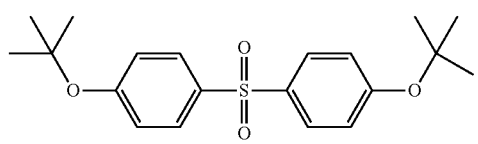
Formula (C-16)
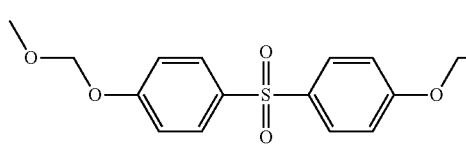
Formula (C-17)
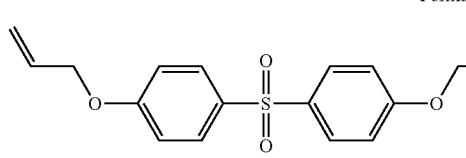
Formula (C-18)
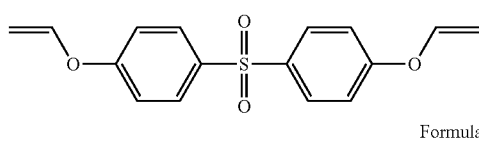
Formula (C-19)
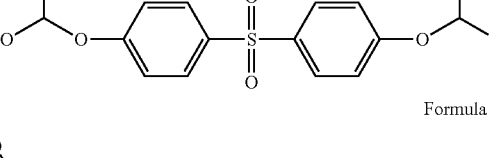
Formula (C-20)
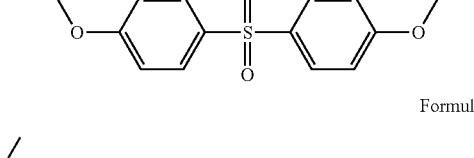
Formula (C-21)
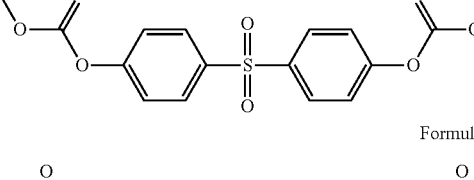
Formula (C-22)
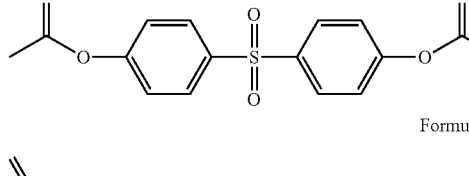
Formula (C-23)
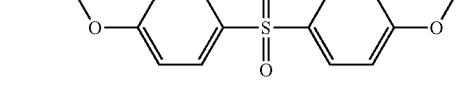

The underlayer film forming composition for lithography of the present invention may contain, besides the components described above, if necessary, organic polymer compounds, photoacid generators, surfactants, and the like.

By using an organic polymer compound, there can be controlled the dry etching rate (a decreased amount of the film thickness per unit time), the attenuation coefficient, the refractive index, and the like of a resist underlayer film formed from the underlayer film forming composition for lithography of the present invention.

The organic polymer compound is not particularly limited and various organic polymers such as condensation polymerization polymers and addition polymerization polymers can be used. As the organic polymer compound, there can be used addition polymerization polymers and condensation polymerization polymers such as polyesters, polystyrenes, polyimides, acrylic polymers, methacrylic polymers, polyvinylethers, phenolnovolacs, naphtholnovolacs, polyethers, polyamides, and polycarbonates. There are preferably used organic polymers having an aromatic ring structure functioning as a light absorbing moiety such as a benzene ring, a naphthalene ring, an anthracene ring, a triazine ring, a quinoline ring, and a quinoxaline ring.

Examples of such an organic polymer compound include addition polymerization polymers containing as a structure unit thereof, an addition polymerizable monomer such as benzyl acrylate, benzyl methacrylate, phenyl acrylate, naphthyl acrylate, anthryl methacrylate, anthrylmethyl methacrylate, styrene, hydroxystyrene, benzyl vinyl ether, and N-phenylmaleimide, and condensation polymerization polymers such as phenolnovolacs and naphtholnovolacs.

When an addition polymerization polymer is used as the organic polymer compound, the polymer compound may be either a homopolymer or a copolymer. For producing the addition polymerization polymer, an addition polymerizable monomer is used.

Examples of such an addition polymerizable monomer include acrylic acid, methacrylic acid, acrylic acid ester compounds, methacrylic acid ester compounds, acrylamide compounds, methacrylamide compounds, vinyl compounds, styrene compounds, maleimide compounds, maleic anhydride, and acrylonitrile.

Examples of the acrylic acid ester compound include methyl acrylate, ethyl acrylate, n-hexyl acrylate, isopropyl acrylate, cyclohexyl acrylate, benzyl acrylate, phenyl acrylate, anthrylmethyl acrylate, 2-hydroxyethyl acrylate, 3-chloro-2-hydroxypropyl acrylate, 2-hydroxypropyl acrylate, 2,2,2-trifluoroethyl acrylate, 2,2,2-trichloroethyl acrylate, 2-bromoethyl acrylate, 4-hydroxybutyl acrylate, 2-methoxyethyl acrylate, tetrahydrofurfuryl acrylate, 5-acryloyloxy-6-hydroxynorbornene-2-carboxylic-6-lactone, 3-acryloxypropyltriethoxysilane, and glycidyl acrylate.

Examples of the methacrylic acid ester compound include methyl methacrylate, ethyl methacrylate, n-hexyl methacrylate, isopropyl methacrylate, cyclohexyl methacrylate, benzyl methacrylate, phenyl methacrylate, anthrylmethyl methacrylate, 2-hydroxyethyl methacrylate, 2-hydroxypropyl methacrylate, 2,2,2-trifluoroethyl methacrylate, 2,2,2-trichloroethyl methacrylate, 2-bromoethyl methacrylate, 4-hydroxybutyl methacrylate, 2-methoxyethyl methacrylate, tetrahydrofurfuryl methacrylate, 5-methacryloyloxy-6-hydroxynorbornene-2-carboxylic-6-lactone, 3-methacryloxypropyltriethoxysilane, glycidyl methacrylate, 2-phenylethyl methacrylate, hydroxyphenyl methacrylate, and bromophenyl methacrylate.

Examples of the acrylamide compound include acrylamide, N-methylacrylamide, N-ethylacrylamide, N-benzylacrylamide, N-phenylacrylamide, N,N-dimethylacrylamide, and N-anthrylacrylamide.

Examples of the methacrylamide compound include methacrylamide, N-methylmethacrylamide, N-ethylmethacrylamide, N-benzylmethacrylamide, N-phenylmethacrylamide, N,N-dimethylmethacrylamide, and N-anthrylacrylamide.

Examples of the vinyl compound include vinyl alcohol, 2-hydroxyethyl vinyl ether, methyl vinyl ether, ethyl vinyl ether, benzyl vinyl ether, vinylacetic acid, vinyltrimethoxysilane, 2-chloroethyl vinyl ether, 2-methoxyethyl vinyl ether, vinylnaphthalene, and vinylanthracene.

Examples of the styrene compound include styrene, hydroxystyrene, chlorostyrene, bromostyrene, methoxystyrene, cyanostyrene, and acetylstyrene.

Examples of the maleimide compound include maleimide, N-methylmaleimide, N-phenylmaleimide, N-cyclohexylmaleimide, N-benzylmaleimide, and N-hydroxyethylmaleimide.

When a condensation polymerization polymer is used as such a polymer, examples of such a polymer include condensation polymerization polymers of a glycol compound and a dicarboxylic acid compound. Examples of the glycol compound include diethylene glycol, hexamethylene glycol, and butylene glycol. Examples of the dicarboxylic acid compound include succinic acid, adipic acid, terephthalic acid, and maleic anhydride. Examples of the polymer also include polyesters, polyamides, and polyimides such as polypyromellitimide, poly(p-phenyleneterephthalamide), polybutylene terephthalate, and polyethylene terephthalate.

When the organic polymer compound contains a hydroxy group, the hydroxy group can effect a crosslinking reaction with a polyorganosiloxane.

As the organic polymer compound, there can be used a polymer compound having a weight average molecular weight of, for example, 1,000 to 1,000,000, or 3,000 to 300,000, or 5,000 to 200,000, or 10,000 to 100,000.

The organic polymer compounds may be used individually or in combination of two or more thereof.

When the organic polymer compound is used, the content thereof is 1 to 200 parts by mass, or 5 to 100 parts by mass, or 10 to 50 parts by mass, or 20 to 30 parts by mass, relative to 100 parts by mass of the condensation product (polyorganosiloxane).

The resist underlayer film forming composition of the present invention may contain an acid generator.

Examples of the acid generator include thermoacid generators and photoacid generators.

The photoacid generator generates an acid during exposure of the resist. Therefore, the acidity of the underlayer film can be controlled. This is one method for adjusting the acidity of the underlayer film to that of the resist as an upper layer of the underlayer film. By adjusting the acidity of the underlayer film, the pattern shape of the resist formed in the upper layer can be controlled.

Examples of the photoacid generator contained in the resist underlayer film forming composition of the present invention include onium salt compounds, sulfonimide compounds, and disulfonyl diazomethane compounds.

Examples of the onium salt compound include: iodonium salt compounds such as diphenyliodoniumhexafluorophosphate, diphenyliodoniumtrifluoromethanesulfonate, diphenyliodoniumnonafluoro normal butane sulfonate, diphenyliodoniumperfluoro normal octane sulfonate, diphenyliodoniumcamphorsulfonate, bis(4-tert-butylphenyl)iodoniumcamphorsulfonate, and bis(4-tert-butylphenyl) iodoniumtrifluoromethanesulfonate; and sulfonium salt compounds such as triphenylsulfoniumhexafluoroantimonate, triphenylsulfoniumnonafluoro normal butane sulfonate, triphenylsulfoniumcamphorsulfonate, and triphenylsulfoniumtrifluoromethanesulfonate.

Examples of the sulfonimide compound include N-(trifluoromethanesulfonyloxy)succinimide, N-(nonafluoro normal butane sulfonyloxy)succinimide, N-(camphorsulfonyloxy)succinimide, and N-(trifluoromethanesulfonyloxy) naphthalimide.

Examples of the disulfonyldiazomethane compound include bis(trifluoromethylsulfonyl)diazomethane, bis(cyclohexylsulfonyl)diazomethane, bis(phenylsulfonyl)diazomethane, bis(p-toluenesulfonyl)diazomethane, bis(2,4-dimethylbenzenesulfonyl)diazomethane, and methylsulfonyl-p-toluenesulfonyldiazomethane.

These photoacid generators may be used individually or in combination of two or more thereof.

When the photoacid generator is used, the content thereof is 0.01 to 5 parts by mass, or 0.1 to 3 parts by mass, or 0.5 to 1 part by mass, relative to 100 parts by mass of the condensation product (polyorganosiloxane).

The surfactant is effective in suppressing the formation of a pin hole, a striation, and the like when the resist underlayer film forming composition for lithography of the present invention is applied onto a substrate.

Examples of the surfactant contained in the resist underlayer film forming composition of the present invention include: nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate, and sorbitan tristearate, polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorinated surfactants, for example, EFTOP EF301, EF303, and EF352 (trade name; manufactured by Tohkem Products Corp.), MEGAFAC F171, F173, R-08, and R-30 (trade name; manufactured by Dainippon Ink & Chemicals Inc.), Fluorad FC430 and FC431 (trade name; manufactured by Sumitomo 3M Limited), AsahiGuard AG710 and Surflon S-382, SC101, SC102, SC103, SC104, SC105, and SC106 (trade names; manufactured by Asahi Glass Co., Ltd.); and Organosiloxane polymer KP341 (manufactured by Shin-Etsu Chemical Co., Ltd.). These surfactants may be used individually or in combination of two or more thereof. When the surfactant is used, the content thereof is 0.0001 to 5 parts by mass, or 0.001 to 1 part by mass, or 0.01 to 0.5 parts by mass, relative to 100 parts by mass of the condensation product (polyorganosiloxane).

In the resist underlayer film forming composition of the present invention, a rheology controlling agent and an adhesion assistant may be blended. The rheology controlling agent is effective in enhancing the fluidity of the underlayer film forming composition. The adhesion assistant is effective in enhancing the adhesion of the underlayer film to the semiconductor substrate or the resist.

The solvent used for the resist underlayer film forming composition of the present invention is not particularly limited to be used so long as the solvent can dissolve the solid content. Examples of such a solvent include methyl cellosolve acetate, ethyl cellosolve acetate, propylene glycol, propylene glycol monomethyl ether, propylene glycol monoethyl ether, methylisobutylcarbinol, propylene glycol monobutyl ether, propylene glycol monomethyl ether acetate, propylene glycol monoethyl ether acetate, propylene glycol monopropyl ether acetate, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethylene glycol monomethyl ether, ethylene glycol monoethyl ether, ethylene glycol monopropyl ether, ethylene glycol monobutyl ether, ethylene glycol monomethyl ether acetate, ethylene glycol monoethyl ether acetate, ethylene glycol monopropyl ether acetate, ethylene glycol monobutyl ether acetate, diethylene glycol dimethyl ether, diethylene glycol diethyl ether, diethylene glycol dipropyl ether, diethylene glycol dibutyl ether, propylene glycol monomethyl ether, propylene glycol dimethyl ether, propylene glycol diethyl ether, propylene glycol dipropyl ether, propylene glycol dibutyl ether, ethyl lactate, propyl lactate, isopropyl lactate, butyl lactate, isobutyl lactate, methyl formate, ethyl formate, propyl formate, isopropyl formate, butyl formate, isobutyl formate, amyl formate, isoamyl formate, methyl acetate, ethyl acetate, amyl acetate, isoamyl acetate, hexyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, isobutyl butyrate, ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-ethoxypropionate, ethyl 3-methoxypropionate, 3-methoxybutyl acetate, 3-methoxypropyl acetate, 3-methyl-3-methoxybutyl acetate, 3-methyl-3-methoxybutyl propionate, 3-methyl-3-methoxybutyl butyrate, methyl acetoacetate, toluene, xylene, methyl ethyl ketone, methyl propyl ketone, methyl butyl ketone, 2-heptanone, 3-heptanone, 4-heptanone, cyclohexanone, N,N-dimethylformamide, N-methylacetamide, N,N-dimethylacetamide, N-methylpyrrolidone, 4-methyl-2-pentanol, and γ-butyrolactone. These solvents may be used individually or in combination of two or more thereof.

Hereinafter, the use of the resist underlayer film forming composition of the present invention is described.

The resist underlayer film forming composition of the present invention is applied onto a substrate used in the production of semiconductor devices (for example, silicon wafer substrates, substrates coated with silicon/silicon dioxide, silicon nitride substrates, glass substrates, ITO substrates, polyimide substrates, substrates coated with a low dielectric constant material (low-k material)) by an appropriate coating method such as a spinner and a coater and then, is baked to form a resist underlayer film. The baking conditions are appropriately selected from baking temperatures of 80° C. to 250° C. and baking time of 0.3 to 60 minutes. Preferably, the baking temperature is 150° C. to 250° C. and the baking time is 0.5 to 2 minutes. Here, the formed underlayer film has a film thickness of, for example, 10 to 1,000 nm, or 20 to 500 nm, or 50 to 300 nm, or 100 to 200 nm.

Next, on the resist underlayer film, for example, a photoresist layer is formed. The formation of the photoresist layer can be performed by a known method, that is, by applying a photoresist composition solution onto the underlayer film and by baking the composition solution. The photoresist has a film thickness of, for example, 50 to 10,000 nm, or 100 to 2,000 nm, or 200 to 1,000 nm.

In the present invention, after the organic underlayer film is formed on the substrate, the resist underlayer film of the present invention can be formed on the organic underlayer film and further, the resist underlayer film can be coated with the photoresist. Thus, even when the pattern width of the photoresist becomes smaller and the resist underlayer film is coated thinly with the photoresist for preventing a pattern collapse, the processing of the substrate becomes possible by selecting an appropriate etching gas. For example, the resist underlayer film of the present invention can be processed with a fluorine-based gas having an etching rate of the resist underlayer film satisfactorily higher than that of the photoresist as an etching gas, and the organic underlayer film can be processed with an oxygen-based gas having an etching rate of the organic underlayer film satisfactorily higher than that of the resist underlayer film of the present invention as an etching gas. Furthermore, the substrate can be processed with a fluorine-based gas having an etching rate of the substrate satisfactorily higher than that of the organic underlayer film as an etching gas.

The photoresist formed on the resist underlayer film of the present invention is not particularly limited so long as the photoresist is sensitive to light used for exposure, and both a negative-type photoresist and a positive-type photoresist can be used. Examples of the photoresist include: a positive-type photoresist made of a novolac resin and 1,2-naphthoquinonediazide sulfonic acid ester; a chemical amplification-type photoresist made of a binder having a group elevating the alkali dissolving rate by being decomposed by an acid, and a photoacid generator; a chemical amplification-type photoresist made of a low molecular compound elevating the alkali dissolving rate of the photoresist by being decomposed by an acid, an alkali-soluble binder, and a photoacid generator; and a chemical amplification-type photoresist made of a binder having a group elevating the alkali dissolving rate by being decomposed by an acid, a low molecular compound elevating the alkali dissolving rate of the photoresist by being decomposed by an acid, and a photoacid generator. Examples of the photoresist include trade name: APEX-E manufactured by Shipley Company, L.L.C., trade name: PAR710 manufactured by Sumitomo Chemical Co., Ltd., and trade name: SEPR430 manufactured by Shin-Etsu Chemical Co., Ltd. The examples also include fluorine atom-containing polymer-based photoresists described in Proc. SPIE, Vol. 3999, 330-334 (2000), Proc. SPIE, Vol. 3999, 357-364 (2000), and Proc. SPIE, Vol. 3999, 365-374 (2000).

Next, the exposure is performed through a predetermined mask. For the exposure, a KrF excimer laser (wavelength: 248 nm), an ArF excimer laser (wavelength: 193 nm), a F2 excimer laser (wavelength: 157 nm), and the like can be used. After exposure, if necessary, post exposure bake can also be performed. The post exposure bake is performed under conditions appropriately selected from baking temperatures of 70° C. to 150° C. and baking time of 0.3 to 10 minutes.

In the present invention, as the resist, a resist for electron beam lithography or a resist for EUV lithography can be used instead of the photoresist. As the electron beam resist, both a positive type and a negative type can be used. Examples of the electron beam resist include: a chemical amplification-type resist made of an acid generator and a binder having a group changing the alkali dissolving rate by being decomposed by an acid; a chemical amplification-type resist made of an alkali-soluble binder, an acid generator, and a low molecular compound changing the alkali dissolving rate of the resist by being decomposed by an acid; a chemical amplification-type resist made of an acid generator, a binder having a group changing the alkali dissolving rate by being decomposed by an acid, and a low molecular compound changing the alkali dissolving rate of the resist by being decomposed by an acid; a non-chemical amplification-type resist made of a binder having a group changing the alkali dissolving rate by being decomposed by an electron beam; and a non-chemical amplification-type resist made of a binder having a moiety changing the alkali dissolving rate by being broken by an electron beam. Also in the case of using the electron beam resist, a resist pattern can be formed in a manner similar to that in the case of using a photoresist, by using an electron beam as the irradiation source.

As the EUV resist, a methacrylate resin-based resist can be used.

Next, the development is performed by a developer (for example, an alkaline developer). Consequently, for example when a positive-type photoresist is used, the photoresist of an exposed part is removed to form a photoresist pattern.

Examples of the developer include alkaline aqueous solutions such as: aqueous solutions of alkali metal hydroxides such as potassium hydroxide and sodium hydroxide; aqueous solutions of quaternary ammonium hydroxides such as tetramethylammonium hydroxide, tetraethylammonium hydroxide, and choline; and aqueous solutions of amines such as ethanolamine, propylamine, and ethylenediamine. Furthermore, in these developers, a surfactant and the like may also be blended. The conditions for development are appropriately selected from temperatures of 5 to 50° C. and time of 10 to 600 seconds.

In the present invention, as the developer, an organic solvent can be used. After exposure, development is performed by a developer (solvent). By development, for example when a positive-type photoresist is used, the photoresist of an unexposed part is removed to form a photoresist pattern.

Examples of the developer include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl 3-methoxypropionate, ethyl 3-methoxypropionate, ethyl 3-ethoxypropionate, and propyl 3-methoxypropionate. Further, in these developers, a surfactant or the like may also be blended. The conditions for development are appropriately selected from temperatures of 5 to 50° C. and time of 10 to 600 seconds.

Then, using the thus formed pattern of the photoresist (upper layer) as a protecting film, the removal of the resist underlayer film (intermediate layer) of the present invention is performed and next, using the film composed of the patterned photoresist and the patterned resist underlayer film (intermediate layer) of the present invention as a protecting film, the removal of the organic underlayer film (underlayer) is performed. Finally, using the patterned resist underlayer film (intermediate layer) of the present invention and the patterned organic underlayer film (underlayer) as a protecting film, the processing of the semiconductor substrate is performed.

First, the resist underlayer film (intermediate layer) of the present invention at the part where the photoresist is removed is removed by dry etching to expose the semiconductor substrate. For dry etching of the resist underlayer film of the present invention, there can be used gases such as tetrafluoromethane ($CF_4$), perfluorocyclobutane ($C_4F_8$), perfluoropropane ($C_3F_8$), trifluoromethane, carbon monoxide, argon, oxygen, nitrogen, sulfur hexafluoride, difluoromethane, nitrogen trifluoride and chlorine trifluoride, chlorine, and trichloroborane and dichloroborane. For dry etching of the resist underlayer film, a halogen-based gas is preferably used. By dry etching with a halogen-based gas, fundamentally, a photoresist that is composed of organic substances is difficult to be removed. On the contrary, the resist underlayer film of the present invention containing a large amount of silicon atoms is immediately removed by a halogen-based gas. Therefore, the decrease of the film thickness of the photoresist according to dry etching of the resist underlayer film can be suppressed. As the result thereof, the photoresist can be used as a thin film. The resist underlayer film is dry-etched preferably with a fluorine-based gas and examples of the fluorine-based gas include tetrafluoromethane ($CF_4$), perfluorocyclobutane ($C_4F_8$), perfluoropropane ($C_3F_8$), trifluoromethane, and difluoromethane ($CH_2F_2$).

Subsequently, using the film composed of the patterned photoresist and the patterned resist underlayer film of the present invention as a protecting film, the removal of the organic underlayer film is performed. The removal of the organic underlayer film (underlayer) is performed by dry etching preferably with an oxygen-based gas. This is because the resist underlayer film of the present invention containing a large amount of silicon atoms is difficult to be removed by dry etching with an oxygen-based gas.

Finally, the processing of the semiconductor substrate is performed. The processing of the semiconductor substrate is performed by dry etching preferably with a fluorine-based gas.

Examples of the fluorine-based gas include tetrafluoromethane ($CF_4$), perfluorocyclobutane ($C_4F_8$), perfluoropropane ($C_3F_8$), trifluoromethane, and difluoromethane ($CH_2F_2$).

As an upper layer of the resist underlayer film of the present invention, an organic anti-reflective coating can be formed before the formation of the photoresist. The anti-reflective coating composition used here is not particularly limited and can be optionally selected from the compositions commonly used in a conventional lithography process to be used. The formation of the anti-reflective coating can be performed by a commonly used method, for example, by applying an anti-reflective coating composition by a spinner or a coater and by baking the composition.

The substrate onto which the resist underlayer film forming composition of the present invention is applied may also be a substrate having an organic or inorganic anti-reflective coating formed by a CVD method on its surface and, on the anti-reflective coating, the underlayer film of the present invention can also be formed.

A resist underlayer film formed from the resist underlayer film forming composition of the present invention may absorb light used in a lithography process depending on the wavelength of light. Then, in such a case, the resist underlayer film can function as an anti-reflective coating having the effect of preventing light reflected on the substrate. Furthermore, the underlayer film of the present invention can also be used as a layer for preventing an interaction between the substrate and the photoresist, a layer having a function of preventing an adverse action of a material used in the photoresist or of a substance generated during exposure of the photoresist against the substrate, a layer having a function of preventing the diffusion of a substance generated in or on the substrate during heating and baking to the upper layer photoresist, a barrier layer for reducing a poisoning effect to the photoresist layer by a semiconductor substrate dielectric layer, and the like.

A resist underlayer film formed from the resist underlayer film forming composition can be applied to a substrate in which a via hole used in the dual damascene process is formed to be used as an embedding material capable of filling the hole without any void. The resist underlayer film can also be used as a planarizing material for planarizing the surface of a semiconductor substrate having unevenness.

In addition, the above resist underlayer film can be used as an underlayer film of an EUV resist also for the following purpose besides the purpose of the function as a hardmask. The above resist underlayer film forming composition can be used as an EUV resist underlayer anti-reflective coating capable of preventing a reflection of exposure light undesirable during EUV exposure (wavelength: 13.5 nm) such as UV and DUV (ArF light and KrF light) on the substrate or the interface without causing intermixing with the EUV resist. The above resist underlayer film forming composition can efficiently prevent light reflection as an underlayer of an EUV resist. When the above resist underlayer film forming composition is used as the EUV resist underlayer film, the process can be performed in a manner similar to that in the case of an underlayer film for a photoresist.

EXAMPLES

Raw Material Monomer Synthesis 1

Into a 100 mL eggplant-shaped flask, 10.00 g (0.05 mol) of N-methylaminopropyltriethoxysilane, 6.54 g (0.06 mol) of triethylamine, and 33.1 g of N,N-dimethylformamide were charged. While the resultant reaction mixture was stirred with a magnetic stirrer, a solvent mixture of 10.59 g (0.05 mol) of 2-chloroethylphenylsulfone and 21.2 g of N,N-dimethylformamide was added dropwise into the reaction mixture. After the completion of the addition, the resultant reaction mixture was heated to 70° C. to effect the reaction for 4 hours. Triethylamine hydrochloride generated by the reaction was removed by filtration. From the filtrate, the solvent was removed using an evaporator, followed by subjecting the resultant concentrate to phase separation using ethyl acetate and water. The resultant organic phase was subjected to a dehydration treatment using magnesium sulfate and was filtered and from the filtered organic phase, ethyl acetate was removed using an evaporator to obtain a crude product. By distilling the crude product under reduced pressure, a compound 1 (of Formula (1-1) in which X is an ethoxy group) which is the objective product was obtained.

$^1$H-NMR (500 MHz): 0.47 ppm (t, 2H), 1.30 ppm (quint, 2H), 2.02 ppm (s, 3H), 2.20 ppm (t, 2H), 2.61 ppm (t, 2H), 3.43-3.49 ppm (m, 11H), 7.64-7.93 ppm (m, 5H)

Raw Material Monomer Synthesis 2

Into a 100 mL eggplant-shaped flask, 5.00 g (0.067 mol) of N-methylallylamine, 9.80 g (0.056 mol) of 4-fluorophenylmethylsulfone, 7.77 g (0.056 mol) of potassium carbonate, and 10.0 g of N-methylpyrrolidone were charged and the resultant reaction mixture was heated to 60° C. to effect the reaction for 8 days. The reaction solution was subjected to phase separation using ethyl acetate and water, and from the resultant organic phase, ethyl acetate was removed using an evaporator to obtain a crude product of an intermediate 1.

Into a 50 mL eggplant-shaped flask, 1.50 g (0.006 mol) of the intermediate 1, 1.18 g (0.007 mol) of triethoxysilane, 0.08 g of a platinum catalyst PI-Pt, and 15 g of toluene were charged and the resultant reaction mixture was subjected to heating-reflux to effect the reaction for 6 hours. From the reaction mixture, the platinum catalyst PI-Pt was removed by filtration and toluene was removed using an evaporator to obtain a crude product. By distilling the crude product under reduced pressure, a compound 2 (of Formula (1-2) in which X is an ethoxy group) which is the objective product was obtained.

$^1$H-NMR (500 MHz): 0.58 ppm (t, 2H), 1.14 ppm (t, 9H), 1.58 ppm (quint, 2H), 2.98 ppm (s, 3H), 3.06 ppm (s, 3H), 3.40 ppm (t, 2H), 3.75 ppm (q, 6H), 6.78-6.80 ppm (m, 2H), 7.61-7.63 ppm (m, 2H)

Synthesis Example 1

15.42 g (70 mol %) of tetraethoxysilane, 4.71 g (25 mol %) of methyltriethoxysilane, 1.05 g (5 mol %) of phenyltrimethoxysilane, and 31.77 g of acetone were charged into a 100 mL flask. While the resultant reaction mixture solution was stirred with a magnetic stirrer, 7.05 g of a 0.01 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The resultant product contained a polymer of Formula (E-1) as a main component, and a hydrolysis product and a monomer. The obtained polymer had a weight average molecular weight measured by GPC of Mw 1,600 in terms of polystyrene.

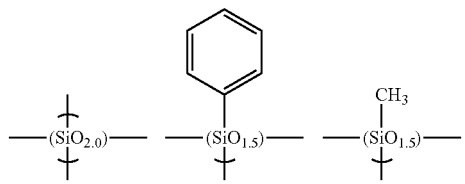

Formula (E-1)

Synthesis Example 2

14.72 g (70 mol %) of tetraethoxysilane, 4.50 g (25 mol %) of methyltriethoxysilane, 2.09 g (5 mol %) of 3-(triethoxysilylpropyl)diallyl isocyanurate, and 31.96 g of acetone were charged into a 100 mL flask. While the resultant reaction mixture solution was stirred with a magnetic stirrer, 6.73 g of a 0.01 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The resultant product contained a polymer of Formula (E-2) as a main component, and a hydrolysis product and a monomer. The obtained polymer had a weight average molecular weight measured by GPC of Mw 1,700 in terms of polystyrene.

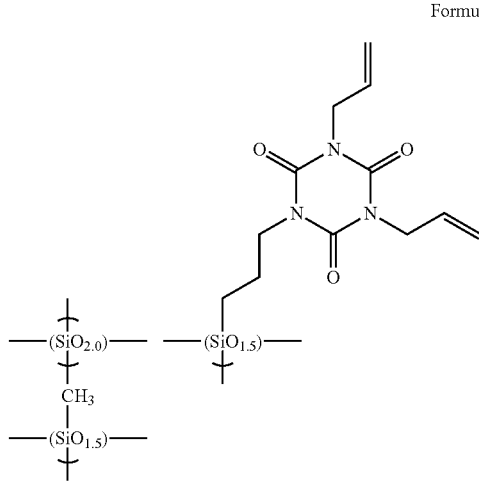

Formula (E-2)

Synthesis Example 3

15.36 g (70 mol %) of tetraethoxysilane, 4.60 g (24.5 mol %) of methyltriethoxysilane, 1.04 g (5 mol %) of phenyltrimethoxysilane, 0.19 g (0.5 mol %) of the compound 1, and 31.79 g of acetone were charged into a 100 mL flask. While the resultant reaction mixture solution was stirred with a magnetic stirrer, 7.02 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (A-1) as a main component, and a hydrolysis product and a monomer. The obtained polymer had a weight average molecular weight measured by GPC of Mw 1,700 in terms of polystyrene.

Synthesis Example 4

14.66 g (70 mol %) of tetraethoxysilane, 4.39 g (24.5 mol %) of methyltriethoxysilane, 2.08 g (5 mol %) of 3-(triethoxysilylpropyl)diallyl isocyanurate, 0.18 g (0.5 mol %) of the compound 1, and 31.79 g of acetone were charged into a 100 mL flask. While the resultant reaction mixture solution was stirred with a magnetic stirrer, 6.70 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (A-2) as a main component, and a hydrolysis product and a monomer. The obtained polymer had a weight average molecular weight measured by GPC of Mw 1,800 in terms of polystyrene.

Synthesis Example 5

15.20 g (70 mol %) of tetraethoxysilane, 3.72 g (20 mol %) of methyltriethoxysilane, 1.03 g (5 mol %) of phenyltrimethoxysilane, 1.26 g (5 mol %) of (4-methoxybenzyl)trimethoxysilane, and 31.83 g of acetone were charged into a 100 mL flask. While the resultant reaction mixture solution was stirred with a magnetic stirrer, 6.95 g of a 0.01 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. The resultant product contained a polymer of Formula (E-3) as a main component, and a hydrolysis product and a monomer. The obtained polymer had a weight average molecular weight measured by GPC of Mw 1,600 in terms of polystyrene.

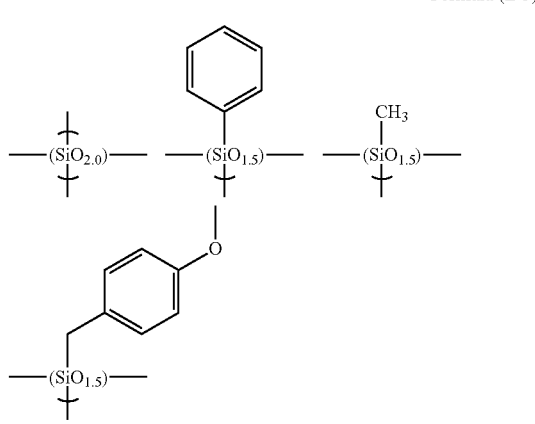

Formula (E-3)

Synthesis Example 6

14.53 g (70 mol %) of tetraethoxysilane, 3.55 g (20 mol %) of methyltriethoxysilane, 2.06 g (5 mol %) of 3-(triethoxysilylpropyl)diallyl isocyanurate, 1.21 g (5 mol %) of (4-methoxybenzyl)trimethoxysilane, and 32.02 g of acetone were charged into a 100 mL flask. While the resultant reaction mixture solution was stirred with a magnetic stirrer, 6.64 g of a 0.01 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. The resultant product contained a polymer of Formula (E-4) as a main component, and a hydrolysis product and a monomer. The obtained polymer had a weight average molecular weight measured by GPC of Mw 1,600 in terms of polystyrene.

Formula (E-4)

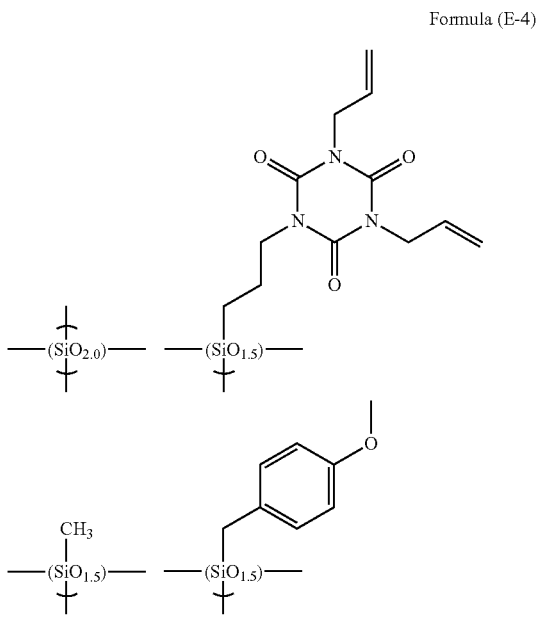

Synthesis Example 7

15.14 g (70 mol %) of tetraethoxysilane, 3.61 g (19.5 mol %) of methyltriethoxysilane, 1.03 g (5 mol %) of phenyltrimethoxysilane, 1.26 g (5 mol %) of (4-methoxybenzyl)trimethoxysilane, 0.19 g (0.5 mol %) of the compound 1, and 31.85 g of acetone were charged into a 100 mL flask. While the resultant reaction mixture solution was stirred with a magnetic stirrer, 6.92 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (A-3) as a main component, and a hydrolysis product and a monomer. The obtained polymer had a weight average molecular weight measured by GPC of Mw 1,700 in terms of polystyrene.

Synthesis Example 8

14.47 g (70 mol %) of tetraethoxysilane, 3.45 g (19.5 mol %) of methyltriethoxysilane, 2.05 g (5 mol %) of 3-(triethoxysilylpropyl)diallyl isocyanurate, 1.20 g (5 mol %) of (4-methoxybenzyl)trimethoxysilane, 0.18 g (0.5 mol %) of the compound 1, and 32.03 g of acetone were charged into a 100 mL flask. While the resultant reaction mixture solution was stirred with a magnetic stirrer, 6.62 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (A-4) as a main component, and a hydrolysis product and a monomer. The obtained polymer had a weight average molecular weight measured by GPC of Mw 1,800 in terms of polystyrene.

Comparative Synthesis Example 1

15.40 g (70 mol %) of tetraethoxysilane, 4.61 g (24.5 mol %) of methyltriethoxysilane, 1.05 g (5 mol %) of phenyltrimethoxysilane, 0.12 g (0.5 mol %) of N-(3-triethoxysilylpropyl)-4,5-dihydroimidazole, and 31.78 g of acetone were charged into a 100 mL flask. While the resultant reaction mixture solution was stirred with a magnetic stirrer, 7.04 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (E-5) as a main component, and a hydrolysis product and a monomer. The obtained polymer had a weight average molecular weight measured by GPC of Mw 1,700 in terms of polystyrene.

Formula (E-5)

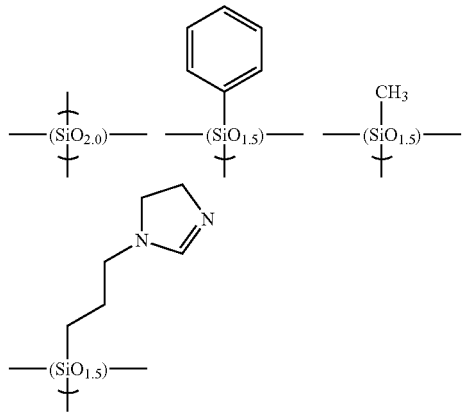

Comparative Synthesis Example 2

15.39 g (70 mol %) of tetraethoxysilane, 4.70 g (25 mol %) of methyltriethoxysilane, 0.94 g (4.5 mol %) of phenyltrimethoxysilane, 0.15 g (0.5 mol %) of 4-methylsulfonyl methylphenyltrimethoxysilane, and 31.78 g of acetone were charged into a 100 mL flask. While the resultant reaction mixture solution was stirred with a magnetic stirrer, 7.04 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (E-6) as a main component, and a hydrolysis product and a monomer. The obtained polymer had a weight average molecular weight measured by GPC of Mw 1,600 in terms of polystyrene.

Formula (E-6)

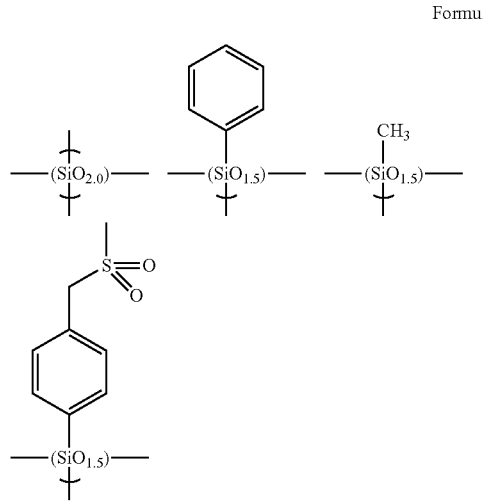

Comparative Synthesis Example 3

15.37 g (70 mol %) of tetraethoxysilane, 4.70 g (25 mol %) of methyltriethoxysilane, 0.94 g (4.5 mol %) of phenyltrimethoxysilane, 0.19 g (0.5 mol %) of 3-(N-triethoxysilyl) propylbenzenesulfonamide, and 31.79 g of acetone were charged into a 100 mL flask. While the resultant reaction mixture solution was stirred with a magnetic stirrer, 7.02 g of a 0.02 mol/L hydrochloric acid was added dropwise into the reaction mixture solution. After the completion of the addition, the flask was transferred into an oil bath adjusted to 85° C., and under warming-reflux, the reaction was effected for 240 minutes. Then, the reaction solution was cooled down to room temperature and to the reaction solution, 21 g of propylene glycol monoethyl ether was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether was added to adjust the resultant solution to contain a solid residue in a proportion of 15% by weight at 140° C. The resultant product contained a polymer of Formula (E-7) as a main component, and a hydrolysis product and a monomer. The obtained polymer had a weight average molecular weight measured by GPC of Mw 1,700 in terms of polystyrene.

Formula (E-7)

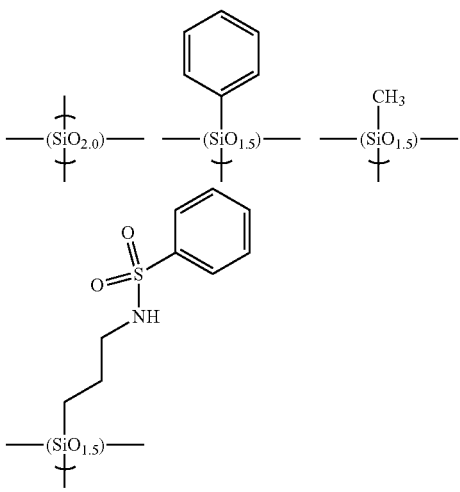

(Preparation of Resist Underlayer Film)

The silicon-containing polymers obtained in Synthesis Example 1 to Synthesis Example 8 were each blended with an acid, a curing catalyst, an additive, a solvent, and water in ratios shown in Table 1. The resultant blend was filtered with a 0.1 μm fluorinated resin filter to prepare each of the solutions of the resist underlayer film forming compositions.

In Table 1, maleic acid is abbreviated as MA; N-(3-triethoxysilylpropyl)-4,5-dihydroimidazole is abbreviated as IMIDTEOS; bisphenol S is abbreviated as BPS; propylene glycol monomethyl ether acetate is abbreviated as PGMEA; and propylene glycol monoethyl ether is abbreviated as PGEE. As the water, ultrapure water was used. Each blending amount is expressed in parts by mass. The blending ratio of the polymer is indicated not as the mass of the polymer solution, but as the mass of the polymer itself.

TABLE 1

| | Polymer | Acid | Curing catalyst | Additive | Solvent | | Water |
|---|---|---|---|---|---|---|---|
| Example 1 | Synthesis Example 1 | MA | Compound 1 | | PGMEA | PGEE | Water |
| (parts by mass) | 2 | 0.06 | 0.012 | | 7 | 80 | 13 |

TABLE 1-continued

| | Polymer | Acid | Curing catalyst | Additive | Solvent | | Water |
|---|---|---|---|---|---|---|---|
| Example 2 | Synthesis Example 2 | MA | Compound 1 | | PGMEA | PGEE | Water |
| (parts by mass) | 2 | 0.06 | 0.012 | | 7 | 80 | 13 |
| Example 3 | Synthesis Example 3 | MA | | | PGMEA | PGEE | Water |
| (parts by mass) | 2 | 0.06 | | | 7 | 80 | 13 |
| Example 4 | Synthesis Example 4 | MA | | | PGMEA | PGEE | Water |
| (parts by mass) | 2 | 0.06 | | | 7 | 80 | 13 |
| Example 5 | Synthesis Example 5 | MA | Compound 1 | | PGMEA | PGEE | Water |
| (parts by mass) | 2 | 0.06 | 0.012 | | 7 | 80 | 13 |
| Example 6 | Synthesis Example 6 | MA | Compound 1 | | PGMEA | PGEE | Water |
| (parts by mass) | 2 | 0.06 | 0.012 | | 7 | 80 | 13 |
| Example 7 | Synthesis Example 7 | MA | | | PGMEA | PGEE | Water |
| (parts by mass) | 2 | 0.06 | | | 7 | 80 | 13 |
| Example 8 | Synthesis Example 8 | MA | | | PGMEA | PGEE | Water |
| (parts by mass) | 2 | 0.06 | | | 7 | 80 | 13 |
| Example 9 | Synthesis Example 1 | MA | Compound 1 | BPS | PGMEA | PGEE | Water |
| (parts by mass) | 2 | 0.06 | 0.012 | 0.025 | 7 | 80 | 13 |
| Example 10 | Synthesis Example 2 | MA | Compound 1 | BPS | PGMEA | PGEE | Water |
| (parts by mass) | 2 | 0.06 | 0.012 | 0.025 | 7 | 80 | 13 |
| Example 11 | Synthesis Example 1 | MA | Compound 2 | | PGMEA | PGEE | Water |
| (parts by mass) | 2 | 0.06 | 0.012 | | 7 | 80 | 13 |
| Example 12 | Synthesis Example 2 | MA | Compound 2 | | PGMEA | PGEE | Water |
| (parts by mass) | 2 | 0.06 | 0.012 | | 7 | 80 | 13 |
| Example 13 | Synthesis Example 5 | MA | Compound 2 | | PGMEA | PGEE | Water |
| (parts by mass) | 2 | 0.06 | 0.012 | | 7 | 80 | 13 |
| Example 14 | Synthesis Example 6 | MA | Compound 2 | | PGMEA | PGEE | Water |
| (parts by mass) | 2 | 0.06 | 0.012 | | 7 | 80 | 13 |
| Comparative Example 1 | Synthesis Example 1 | MA | BTEAC | | PGMEA | PGFF | Water |
| (parts by mass) | 2 | 0.06 | 0.012 | | 7 | 80 | 13 |
| Comparative Example 2 | Synthesis Example 2 | MA | BTEAC | | PGMFA | PGFF | Water |
| (parts by mass) | 2 | 0.06 | 0.012 | | 7 | 80 | 13 |
| Comparative Example 3 | Synthesis Example 1 | MA | IMIDTEOS | | PGMFA | PGFF | Water |
| (parts by mass) | 2 | 0.06 | 0.012 | | 7 | 80 | 13 |
| Comparative Example 4 | Synthesis Example 2 | MA | IMIDTEOS | | PGMFA | PGFF | Water |
| (parts by mass) | 2 | 0.06 | 0.012 | | 7 | 80 | 13 |
| Comparative Example 5 | Comparative Synthesis Example 1 | MA | | | PGMEA | PGEE | Water |
| (parts by mass) | 2 | 0.06 | | | 7 | 80 | 13 |

TABLE 1-continued

| | Polymer | Acid | Curing catalyst | Additive | Solvent | | Water |
|---|---|---|---|---|---|---|---|
| Comparative Example 6 | Comparative Synthesis Example 2 | MA | | | PGMEA | PGEE | Water |
| (parts by mass) | 2 | 0.06 | | | 7 | 80 | 13 |
| Comparative Example 7 | Comparative Synthesis Example 3 | MA | | | PGMEA | PGEE | Water |
| (parts by mass) | 2 | 0.06 | | | 7 | 80 | 13 |

(Solvent Resistance Test)

The resist underlayer film forming compositions in Example 1 to Example 14 and Comparative Example 1 to Comparative Example 7 were each applied onto corresponding silicon wafers by a spin coating method. The composition was baked on a hot plate at 240° C. for 1 minute to form a resist underlayer film. Then, the resist underlayer film was immersed in propylene glycol monomethyl ether acetate (PGMEA) used as a solvent for an over coating resist composition for 1 minute. When the change in the film thickness of the resist underlayer film between before and after the immersion was 1 nm or less, it was determined as "favorable (O)" whereas when the change in the film thickness was more than 1 nm, it was determined as "failed (x)". The obtained result is shown in Table 2.

(Measurement of Optical Constants)

The Si-containing resist underlayer film forming compositions prepared in Examples 1 to 14 and Comparative Examples 1 to 7 were each applied onto corresponding silicon wafers using a spinner. The composition was heated on a hot plate at 200° C. for 1 minute to form a Si-containing resist underlayer film (film thickness: 0.05 μm). Then, the refractive index (n value) and the optical absorptivity (k value; also called the attenuation coefficient) at a wavelength of 193 nm of the resist underlayer film were measured using a spectro-ellipsometer (VUV-VASE VU-302; manufactured by J.A.Woollam Co., Inc.).

(Measurement of Dry Etching Rate)

Etchers and etching gases used in the measurement of dry etching rates were as follows:
ES401 (manufactured by Nippon Scientific Co., Ltd.): $CF_4$
RIE-10NR (manufactured by Samco, Inc.): $O_2$.

The solutions of the Si-containing resist underlayer film forming compositions prepared in Examples 1 to 14 and Comparative Examples 1 to 7 were each applied onto corresponding silicon wafers using a spinner. The solution was heated on a hot plate at 240° C. for 1 minute to form Si-containing resist underlayer films (film thickness: 0.08 μm (for measurement of etching rate with $CF_4$ gas), and 0.05 μm (for measurement of etching rate with $O_2$ gas)). In a similar manner, organic underlayer film forming compositions listed below were each applied onto corresponding silicon wafers using a spinner to form coating films thereon. By using $O_2$ gas as the etching gas, the dry etching rate of the organic underlayer film was measured. The dry etching rates of the Si-containing resist underlayer films of Examples 1 to 14 and Comparative Examples 1 to 7 are compared.

Shown are the solvent resistance against propylene glycol monomethyl ether acetate (PGMEA), the refractive index n at a wavelength of 193 nm, the optical absorptivity k at a wavelength of 193 nm, the etching rate (nm/min) with a fluorine-based gas ($CF_4$ gas), and the resistance against an oxygen-based gas ($O_2$ gas) that is indicated as the etching rate ratio of (resist underlayer film of the present invention)/(organic underlayer film).

TABLE 2

| | Solvent resistance | Refractive index | Optical absorptivity | Etching rate with fluorine-based gas | Oxygen-based gas resistance |
|---|---|---|---|---|---|
| Example 1 | O | 1.63 | 0.11 | 19.9 | 0.01 |
| Example 2 | O | 1.64 | 0.08 | 21.7 | 0.02 |
| Example 3 | O | 1.63 | 0.11 | 20.1 | 0.01 |
| Example 4 | O | 1.64 | 0.08 | 21.2 | 0.02 |
| Example 5 | O | 1.61 | 0.24 | 22.6 | 0.02 |
| Example 6 | O | 1.63 | 0.19 | 24.5 | 0.03 |
| Example 7 | O | 1.63 | 0.24 | 21.6 | 0.01 |
| Example 8 | O | 1.63 | 0.18 | 20.0 | 0.03 |
| Example 9 | O | 1.62 | 0.16 | 20.0 | 0.02 |
| Example 10 | O | 1.63 | 0.11 | 22.5 | 0.02 |
| Example 11 | O | 1.63 | 0.11 | 19.3 | 0.01 |
| Example 12 | O | 1.64 | 0.08 | 20.6 | 0.02 |
| Example 13 | O | 1.61 | 0.24 | 21.4 | 0.02 |
| Example 14 | O | 1.63 | 0.19 | 23.7 | 0.03 |
| Comparative Example 1 | O | 1.63 | 0.12 | 19.4 | 0.01 |
| Comparative Example 2 | O | 1.64 | 0.08 | 21.4 | 0.02 |
| Comparative Example 3 | O | 1.63 | 0.11 | 19.4 | 0.01 |
| Comparative Example 4 | O | 1.64 | 0.07 | 21.4 | 0.02 |
| Comparative Example 5 | O | 1.64 | 0.08 | 19.4 | 0.02 |
| Comparative Example 6 | O | 1.62 | 0.12 | 20.8 | 0.01 |
| Comparative Example 7 | O | 1.62 | 0.12 | 21.5 | 0.02 |

(Preparation of Organic Resist Underlayer Film)

In nitrogen, into a 100 mL four-neck flask, carbazole (6.69 g, 0.040 mol, manufactured by Tokyo Chemical Industry Co., Ltd.), 9-fluorenone (7.28 g, 0.040 mol, manufactured by Tokyo Chemical Industry Co., Ltd.), and p-toluenesulfonic acid monohydrate (0.76 g, 0.0040 mol, manufactured by Tokyo Chemical Industry Co., Ltd.) were charged and thereto, 1,4-dioxane (6.69 g, manufactured by Kanto Chemical Co., Inc.) was added, followed by stirring the resultant reaction mixture. The temperature of the reaction mixture was elevated to 100° C. to dissolve the reaction mixture and the polymerization was initiated. After 24 hours, the reaction mixture was left to be cooled down to 60° C., and then, to the reaction mixture, chloroform (34 g, manufactured by Kanto Chemical Co., Inc.) was added to dilute the reaction mixture, followed by reprecipitating the resultant reaction mixture in methanol (168 g, manufactured by Kanto Chemical Co., Inc.). The obtained precipitate was filtered and was dried using a vacuum drier at 80° C. for 24 hours to obtain 9.37 g of the objective polymer (Formula (F-1), hereinafter abbreviated as PCzFL).

Formula (F-1)

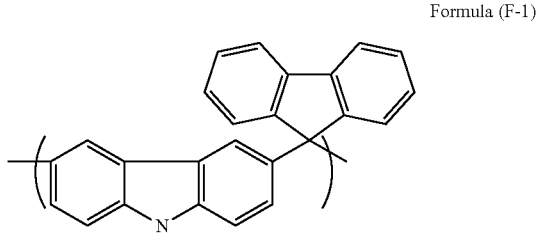

The measurement result of $^1$H-NMR of PCzFL was as follows:

$^1$H-NMR (400 MHz, DMSO-$d_6$): δ7.03-7.55 (br, 12H), δ7.61-8.10 (br, 4H), δ11.18 (br, 1H).

PCzFL had a weight average molecular weight Mw of 2,800 and a polydispersity Mw/Mn of 1.77 that were measured by GPC in terms of polystyrene.

With 20 g of the obtained resin, 3.0 g of tetramethoxymethyl glycoluril (trade name: POWDER LINK 1174; manufactured by Mitsui Cytec Ltd.) as a crosslinker, 0.30 g of pyridinium p-toluenesulfonate as a catalyst, and 0.06 g of MEGAFAC R-30 (trade name; manufactured by Dainippon Ink & Chemicals Inc.) as a surfactant were mixed. The resultant mixture was dissolved in 88 g of propylene glycol monomethyl ether acetate to prepare a solution. The solution was then filtered using a polyethylene microfilter having a pore diameter of 0.10 μm and was further filtered using a polyethylene microfilter having a pore diameter of 0.05 μm to prepare a solution of an organic resist underlayer film forming composition to be used for a lithography process with a multilayer film.

(Resist Patterning Evaluation)

The organic underlayer film (layer A) forming composition obtained in the above formula was applied onto a silicon wafer, and the composition was baked on a hot plate at 240° C. for 60 seconds to obtain an organic underlayer film (layer A) having a film thickness of 200 nm. The Si-containing resist underlayer film (layer B) forming compositions obtained in Example 1 to Example 10 and Comparative Example 1 to Comparative Example 7 were each applied onto the corresponding organic underlayer films (layers A). The composition was baked on a hot plate at 240° C. for 45 seconds to obtain a Si-containing resist underlayer film (layer B). The Si-containing resist underlayer films (layers B) had a film thickness of 45 nm.

(Development with Alkaline Developer•PTD)

Onto each of the layers B, a commercially available photoresist solution (trade name: AR 2772; manufactured by JSR Corporation) was applied by a spinner, and the solution was baked on a hot plate at 110° C. for 60 seconds to form a photoresist film (layer C) having a film thickness of 120 nm. The patterning of the resist was performed using an ArF exposing machine S-307E, manufactured by Nikon Corporation (wavelength: 193 nm, NA, σ: 0.85, 0.93/0.85 (Dipole), immersion liquid: water). The target was a photoresist after the development having a line width and a width between lines of 0.065 μm each, which is what is called lines and spaces (dense lines), and the exposure was performed through a mask set to form such a photoresist.

Then, the resultant product was baked on a hot plate at 110° C. for 60 seconds, was cooled down, and was developed with a tetramethylammonium hydroxide aqueous solution (developer) having a concentration of 2.38% by mass in a 60-second single paddle process. With respect to the obtained photoresist patterns, a photoresist pattern in which no large pattern peeling, no undercut, or no widening (footing) at a line bottom was caused was evaluated as favorable.

TABLE 3

| | |
|---|---|
| Example 1 | Favorable |
| Example 2 | Favorable |
| Example 3 | Favorable |
| Example 4 | Favorable |
| Example 5 | Favorable |
| Example 6 | Favorable |
| Example 7 | Favorable |
| Example 8 | Favorable |
| Example 9 | Favorable |
| Example 10 | Favorable |
| Example 11 | Favorable |
| Example 12 | Favorable |
| Example 13 | Favorable |
| Example 14 | Favorable |
| Comparative Example 1 | Failed (footing) |
| Comparative Example 2 | Failed (footing) |
| Comparative Example 3 | Failed (footing) |
| Comparative Example 4 | Failed (footing) |
| Comparative Example 5 | Failed (footing) |
| Comparative Example 6 | Failed (large peeling) |
| Comparative Example 7 | Failed (footing) |

(Development with Organic Solvent•NTD)

Onto each of the layers B, a commercially available photoresist solution (trade name: FAiRS-9521NT05; manufactured by FUJIFILM Corporation) was applied by a spinner and the solution was heated on a hot plate at 100° C. for 1 minute to form photoresist films (layers C) having a film thickness of 85 nm.

Subsequently, using an NSR-S307E scanner (manufactured by Nikon Corporation (wavelength: 193 nm, NA, σ: 0.85, 0.93/0.85), exposure was performed through a mask set to form a photoresist after the development having a line width and a width between lines of 0.065 μm each, that is, a dense line of 0.065 μm line and space (L/S)=1/1, and through a mask set to form a photoresist after the development having a line width and a width between lines of 0.060 μm each, that is, a dense line of 0.060 μm line and space (L/S)=1/1. Then, the resist pattern was baked on a hot plate at 100° C. for 60 seconds, was cooled down, and was developed using butyl acetate (solvent developer) for 60 seconds to form a negative-type pattern on the resist underlayer film (layer B).

With respect to the obtained photoresist patterns, a photoresist pattern in which no large pattern peeling, no undercut, or no widening (footing) at a line bottom was caused was evaluated as favorable.

TABLE 4

| | Width and Interval in Pattern 0.065 μm | Width and Interval in Pattern 0.060 μm |
|---|---|---|
| Example 1 | Favorable | Favorable (partial peeling) |
| Example 3 | Favorable | Favorable (partial peeling) |
| Example 5 | Favorable | Favorable |
| Example 7 | Favorable | Favorable |
| Example 11 | Favorable | Favorable |

TABLE 4-continued

| | Width and Interval in Pattern 0.065 μm | Width and Interval in Pattern 0.060 μm |
|---|---|---|
| Example 13 | Favorable | (partial peeling) Favorable |
| Comparative Example 1 | Favorable (partial peeling) | Failed (large peeling) |
| Comparative Example 3 | Favorable (partial peeling) | Failed (large peeling) |
| Comparative Example 5 | Favorable (partial peeling) | Failed (large peeling) |
| Comparative Example 6 | Favorable (partial peeling) | Failed (footing) |
| Comparative Example 7 | Failed (large peeling) | Failed (large peeling) |

INDUSTRIAL APPLICABILITY

To provide a resist underlayer film forming composition for forming a resist underlayer film capable of processing a substrate by forming a rectangular pattern. The resist underlayer film forming composition can be utilized as a resist underlayer film forming composition for lithography for forming a resist underlayer film capable of being used as a hardmask. The resist underlayer film forming composition causes no intermixing with an over coating resist. The resist underlayer film forming composition has a dry etching rate larger than that of a resist with respect to a fluorine-based etching gas, so that a resist pattern can be transferred to the resist underlayer film of the present application, and exhibits etching resistance against an oxygen-based etching gas, so that a resist pattern can be transferred to an organic underlayer film.

The invention claimed is:

1. A composition comprising:
    as a silane, a hydrolyzable organosilane, a hydrolysis product of the hydrolyzable organosilane, a hydrolysis-condensation product of the hydrolyzable organosilane, or a combination thereof, wherein
        the hydrolyzable organosilane comprises a combination of at least one silane compound selected from the group consisting of a silane compound of Formula (1-a) and a silane compound of Formula (1-b):

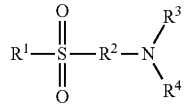

Formula (1-a)

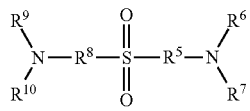

Formula (1-b)

wherein in Formula (1-a),
    at least one group among $R^1$, $R^3$, and $R^4$ is a group in which a —Si(X)$_3$ group is bonded to a terminal of a $C_{1\text{-}10}$ alkylene group, and other group(s) among $R^1$, $R^3$, and $R^4$ is(are) a hydrogen atom, a $C_{1\text{-}10}$ alkyl group, or a $C_{6\text{-}40}$ aryl group;
    $R^2$ is a $C_{1\text{-}10}$ alkylene group or a $C_{6\text{-}40}$ arylene group; and
    X is an alkoxy group, an acyloxy group, or a halogen atom, wherein $R^3$ and $R^4$ are not simultaneously hydrogen atoms;

in Formula (1-b),
    at least one group among $R^6$, $R^7$, $R^9$, and $R^{10}$ is a group in which a —Si(X)$_3$ group is bonded to a terminal of a $C_{1\text{-}10}$ alkylene group, and other group(s) among $R^6$, $R^7$, $R^9$, and $R^{10}$ is(are) a hydrogen atom, a $C_{1\text{-}10}$ alkyl group, or a $C_{6\text{-}40}$ aryl group;
    $R^5$ and $R^8$ are each a $C_{1\text{-}10}$ alkylene group or a $C_{6\text{-}40}$ arylene group; and
    X is an alkoxy group, an acyloxy group, or a halogen atom,
with at least one organic silicon compound selected from the group consisting of an organic silicon compound of Formula (3):

Formula (3)

wherein in Formula (3),
    $R^{21}$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, a cyano group, or a combination of these groups, and is bonded to a silicon atom through a Si—C bond;
    $R^{22}$ is an alkoxy group, an acyloxy group, or a halogen atom; and
    a is an integer of 0 to 3,
and an organic silicon compound of Formula (4):

Formula (4)

wherein in Formula (4),
    $R^{31}$ is an alkyl group;
    $R^{32}$ is an alkoxy group, an acyloxy group, or a halogen atom;
    Y is an alkylene group or an arylene group;
    b is an integer of 0 or 1; and
    c is an integer of 0 or 1.

2. A resist underlayer film forming composition for lithography, comprising:
    as a silane, a hydrolyzable organosilane, a hydrolysis product of the hydrolyzable organosilane, a hydrolysis-condensation product of the hydrolyzable organosilane, or a combination thereof, wherein
        the hydrolyzable organosilane comprises a combination of at least one silane compound selected from the group consisting of a silane compound of Formula (1-a) and a silane compound Formula (1-b):

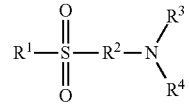

Formula (1-a)

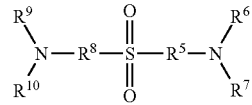

Formula (1-b)

wherein in Formula (1-a),
    at least one group among $R^1$, $R^3$, and $R^4$ is a group in which a —Si(X)$_3$ group is bonded to a terminal of a $C_{1\text{-}10}$ alkylene group, and other group(s) among $R^1$, $R^3$, and $R^4$ is(are) a hydrogen atom, a $C_{1\text{-}10}$ alkyl group, or a $C_{6\text{-}40}$ aryl group;

$R^2$ is a $C_{1-10}$ alkylene group or a $C_{6-40}$ arylene group; and

X is an alkoxy group, an acyloxy group, or a halogen atom, wherein $R^3$ and $R^4$ are not simultaneously hydrogen atoms;

in Formula (1-b), at least one group among $R^6$, $R^7$, $R^9$, and $R^{10}$ is a group in which a —Si(X)$_3$ group is bonded to a terminal of a $C_{1-10}$ alkylene group, and other group(s) among $R^6$, $R^7$, $R^9$, and $R^{10}$ is(are) a hydrogen atom, a $C_{1-10}$ alkyl group, or a $C_{6-40}$ aryl group;

$R^5$ and $R^8$ are each a $C_{1-10}$ alkylene group or a $C_{6-40}$ arylene group; and X is an alkoxy group, an acyloxy group, or a halogen atom, with at least one organic silicon compound selected from the group consisting of an organic silicon compound of Formula (3):

    Formula (3)

wherein in Formula (3), $R^{21}$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, a cyano group, or a combination of these groups, and is bonded to a silicon atom through a Si—C bond;

$R^{22}$ is an alkoxy group, an acyloxy group, or a halogen atom; and a is an integer of 0 to 3, and an organic silicon compound of Formula (4):

    Formula (4)

wherein in Formula (4), $R^{31}$ is an alkyl group;

$R^{32}$ is an alkoxy group, an acyloxy group, or a halogen atom;

Y is an alkylene group or an arylene group;

b is an integer of 0 or 1; and c is an integer of 0 or 1.

3. The resist underlayer film forming composition according to claim 2, wherein the silane compound of Formula (1-a) is a silane compound of Formula (2):

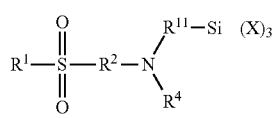    Formula (2)

wherein in Formula (2), $R^1$ and $R^4$ are each a hydrogen atom, a $C_{1-10}$ alkyl group, or a $C_{6-40}$ aryl group;

$R^2$ is a $C_{1-10}$ alkylene group or a $C_{6-40}$ arylene group;

$R^{11}$ is a $C_{1-10}$ alkylene group; and X is an alkoxy group, an acyloxy group, or a halogen atom.

4. The composition according to claim 2, wherein at least one hydrolysis-condensation product of the silane compound of Formula (1-a) or Formula (1-b) with an organic silicon compound of Formula (3) is contained as a polymer.

5. The composition according to claim 2, further comprising an acid.

6. The composition according to claim 2, further comprising water.

7. A resist underlayer film obtained by applying the resist underlayer film forming composition as claimed in claim 2 onto a semiconductor substrate, and baking the composition.

8. A method for producing a semiconductor device, the method comprising:

applying the resist underlayer film forming composition as claimed in claim 2 onto a semiconductor substrate and baking the composition to form a resist underlayer film;

applying a composition for a resist onto the resist underlayer film to form a resist film;

exposing the resist film to light;

developing the resist film after the exposing to obtain a patterned resist film;

etching the resist underlayer film according to a pattern of the patterned resist film; and processing the semiconductor substrate according to a pattern of the resist film and the resist underlayer film.

9. A method for producing a semiconductor device, the method comprising:

forming an organic underlayer film on a semiconductor substrate;

applying the resist underlayer film forming composition as claimed in claim 2, onto the organic underlayer film and baking the composition to form a resist underlayer film;

applying a composition for a resist onto the resist underlayer film to form a resist film;

exposing the resist film to light;

developing the resist film after the exposing to obtain a patterned resist film;

etching the resist underlayer film according to a pattern of the patterned resist film;

etching the organic underlayer film according to a pattern of the pattered resist underlayer film; and processing the semiconductor substrate according to a pattern of the patterned organic underlayer film.

* * * * *